(12) United States Patent
Hirose

(10) Patent No.: US 7,841,979 B2
(45) Date of Patent: Nov. 30, 2010

(54) OBSERVATION SYSTEM

(75) Inventor: Kenji Hirose, Tokyo (JP)

(73) Assignee: Olympus Corporation (JP)

( * ) Notice: Subject to any disclaimer, the term of this patent is extended or adjusted under 35 U.S.C. 154(b) by 1083 days.

(21) Appl. No.: 10/860,762

(22) Filed: Jun. 3, 2004

(65) Prior Publication Data

US 2004/0246469 A1 Dec. 9, 2004

(30) Foreign Application Priority Data

Jun. 5, 2003 (JP) .............................. 2003-161072
May 28, 2004 (JP) .............................. 2004-158912

(51) Int. Cl.
*A61B 1/00* (2006.01)
(52) U.S. Cl. ...................... 600/102; 600/101; 600/103; 606/1; 248/122.1; 248/124.1; 248/125.1
(58) Field of Classification Search ................ 600/102, 600/103; 606/1; 248/122.1, 124.1
See application file for complete search history.

(56) References Cited

U.S. PATENT DOCUMENTS

| | | | |
|---|---|---|---|
| 5,173,802 A * | 12/1992 | Heller ......................... | 359/384 |
| 5,697,939 A * | 12/1997 | Kubota et al. ............... | 606/130 |
| 5,818,638 A * | 10/1998 | Nakamura .................. | 359/384 |
| 5,824,007 A * | 10/1998 | Faraz et al. ................. | 606/130 |
| 5,825,536 A * | 10/1998 | Yasunaga et al. ............ | 359/384 |
| 6,106,511 A * | 8/2000 | Jensen .......................... | 606/1 |
| 6,368,332 B1 * | 4/2002 | Salcudean et al. ........... | 606/130 |
| 6,419,626 B1 * | 7/2002 | Yoon ........................... | 600/109 |
| 6,514,239 B2 * | 2/2003 | Shimmura et al. ............ | 606/1 |
| 6,702,805 B1 * | 3/2004 | Stuart ............................ | 606/1 |
| 2001/0027313 A1 * | 10/2001 | Shimmura et al. ............ | 606/1 |

FOREIGN PATENT DOCUMENTS

| | | |
|---|---|---|
| JP | 6-17940 | 3/1994 |
| JP | 10-248796 | 9/1998 |
| JP | 11-290339 | 10/1999 |

(Continued)

OTHER PUBLICATIONS

Japanese Office Action mailed Feb. 9, 2010 in connection with corresponding Japanese Patent Application No. 2004-158912.

(Continued)

*Primary Examiner*—Matthew J Kasztejna
(74) *Attorney, Agent, or Firm*—Ostrolenk Faber LLP

(57) ABSTRACT

An observation system includes an observation device, an image pickup device, a display device, and at least one holding device. The observation device includes an optical objective system for observing an object. The image pickup device is capable of picking up an optical image incident upon the optical objective system of the observation device. The display device is capable of displaying the image picked up by the image pickup device. The holding device includes a moving mechanism which holds the observation device and the display device and which moves one of the observation device and the display device in conjunction with movement of the other device, and a switching mechanism capable of switching the observation device and the display device to a state in which the devices are movable by the moving mechanism and a state in which the devices are fixable in positions moved by the moving mechanism.

58 Claims, 14 Drawing Sheets

FOREIGN PATENT DOCUMENTS

| | | |
|---|---|---|
| JP | 11-319936 | 11/1999 |
| JP | 2001-51201 | 2/2001 |
| JP | 2001-258903 | 9/2001 |
| JP | 2002-17751 | 1/2002 |

OTHER PUBLICATIONS

English translation of Japanese Office Action issued in connection with corresponding Japanese application provided as an explanation of prior art relevancy.

* cited by examiner

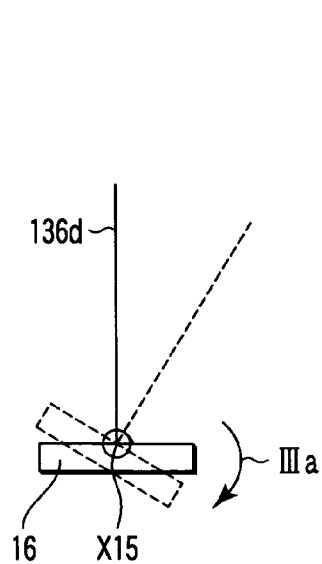
F I G. 13A
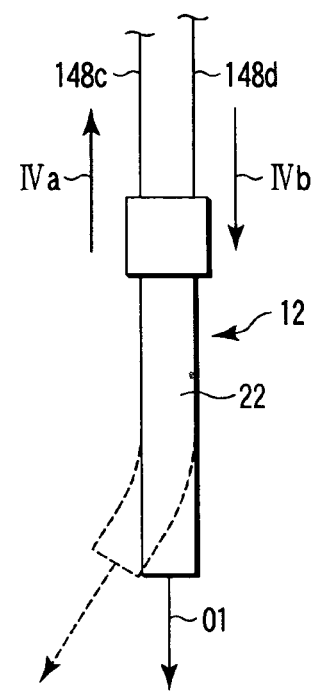
F I G. 13B
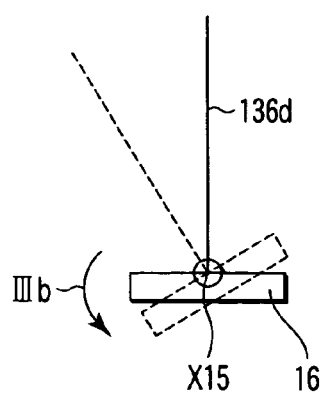
F I G. 14A
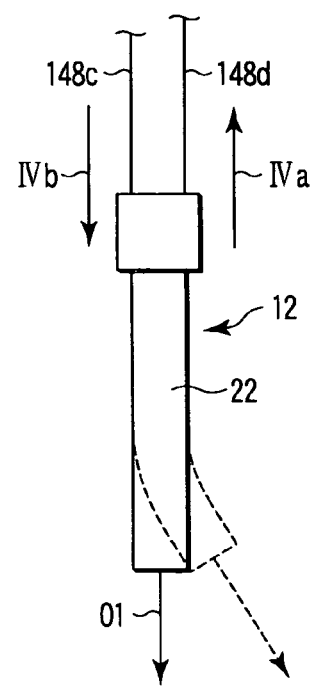
F I G. 14B

OBSERVATION SYSTEM

CROSS-REFERENCE TO RELATED APPLICATIONS

This application is based upon and claims the benefit of priority from prior Japanese Patent Applications No. 2003-161072, filed Jun. 5, 2003; and No. 2004-158912, filed May 28, 2004, the entire contents of both of which are incorporated herein by reference.

BACKGROUND OF THE INVENTION

1. Field of the Invention

The present invention relates to an observation system for use in operation of a fine portion, for example, in neurosurgery.

2. Description of the Related Art

In general, an endoscope is used in a surgical operation or the like for a reason that there is little invasion with respect to a patient. In the operation using the endoscope, an insertion section of the endoscope is inserted into an operative part from various angles or directions depending on the position of the operative part. An endoscopic image of the operative part which cannot be directly observed by an operator is reflected in a monitor installed before the operator. The operator performs diagnosis or treatment while confirming the endoscopic image.

In general, a curved tube is disposed in a distal portion of the insertion section of the endoscope as described, for example, in Jpn. Pat. Appln. KOKAI Publication No. 10-248796. With the curved tube, a view field direction of the insertion section of the endoscope is easily changeable by a hand operation portion, even when the insertion section is inserted in a body.

Additionally, to perform a fine operation in neurosurgery or the like, a binocular microscope has heretofore been used, with which stereoscopic vision is possible. In recent years, a video type stereoscopic microscope has been proposed in which an image pickup section is disposed independently of a display section as described in Jpn. Pat. Appln. KOKAI Publication No. 2001-51201 for a reason that an advice can be given from a remote place or people can simultaneously perform stereoscopic observation. The endoscopic system or the video type stereoscopic microscope has the following problem, because the image pickup section independently moves with respect to the display section.

In general, in the endoscopic operation, the operative part can be observed from various angles using the endoscope. Since the monitor is usually fixed in a predetermined position with respect to the operative part, a direction of operator's eyes toward the monitor does not match an observation direction of the endoscope. Even when the observation direction of the endoscope. Even when the observation direction of the endoscope is changed, video of the endoscope simply moves on the monitor. Therefore, the operator does not easily recognize the position or the direction of the operative part with respect to the endoscope.

The operator needs to perform treatment or observation while constantly imagining a positional relation between the endoscope and the operative part, and experiences and skills are required. When the endoscope described, for example, in the Jpn. Pat. Appln. KOKAI Publication No. 10-248796 is used, and the observation direction is changed by a curved portion disposed in the distal portion of the insertion section of the endoscope, the operator cannot visually observe a curving degree. Therefore, it becomes more difficult to precisely grasp the observation direction of the endoscope.

Similarly even in the video stereoscopic microscope, the direction of the operator's eyes with respect to the monitor does not match the observation direction of the image pickup section, and the video simply moves on the monitor, even when the observation direction of the image pickup section is changed. Therefore, the position or the direction of the operative part observed by the image pickup section is not easily recognized, the operator needs to perform the treatment or observation while constantly imagining section and the operative part, and the experiences and skills are required.

For example, a device described in Jpn. Pat. Publication No. 6-17940 or Jpn. Pat. Appln. KOKAI Publication No. 2002-17751 can solve the problem.

For example, an endoscope direction display device described in the Jpn. Pat. Publication No. 6-17940 includes: an insertion hole for passing an insertion tube portion of an endoscope; light emitting means for emitting light inwards from multiple directions of an inner periphery of the insertion hole; light reflection means formed on an insertion tube outer peripheral surface of the endoscope; and a plurality of light receiving means arranged inwards from multiple directions of the insertion hole inner periphery. Therefore, the light from the light emitting means, reflected by the light reflection means, is received, distribution of received lights is measured to determine a rotation direction of the endoscope during the rotation, and display on the monitor is possible.

An operation navigation device described, for example, in the Jpn. Pat. Appln. KOKAI Publication No. 2002-17751 includes: instrumentation means for measuring three-dimensional position/posture of the patient with surgical equipments such as the endoscope and treatment tool; and addition means for extracting patient's tomographic image information based on measured three-dimensional position/posture information to add the three-dimensional position/posture information to the extracted tomographic image information. The operation navigation device further includes measurement means for measuring a distance between the patient and the endoscope or the treatment tool. The three-dimensional position/posture information is added to the tomographic image information together with distance information by distance measurement of the measurement means. Therefore, the operator can easily grasp the positional relation between the surgical equipment and the operative part, and it is possible to quickly guide the surgical equipment to a target position.

BRIEF SUMMARY OF THE INVENTION

According to an aspect of the present invention, there is provided an observation system including:

an observation device including an optical objective system for observation of an object;

an image pickup device which picks up an optical image incident upon the optical objective system of the observation device;

a display device which is electrically connected to the image pickup device and which displays the optical image picked up by the image pickup device; and at least one holding mechanism including a moving mechanism which holds the observation device and the display device and which moves one of the observation device and the display device in conjunction with movement of the other device, and a switching mechanism capable of switching the observation device and the display device to a state in which the devices are movable by the moving mechanism and a state in which the devices are fixable in positions moved by the moving mechanism.

Advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 13A is a schematic diagram showing that the monitor in the observation system according to the fifth embodiment is observed from an arrow γ direction shown in FIG. 10, a solid line shows the parallel state of the monitor with respect to the floor surface, and a broken line shows a state in which the monitor is rotated in an arrow IIIa direction;

FIG. 13B is a schematic diagram of the insertion section of the endoscope in the observation system according to the fifth embodiment, a solid line shows a state in which the insertion section of the endoscope crosses the floor surface at right angles, and a broken line shows a curved state of a curved portion of the insertion section of the endoscope, curved in conjunction at a time when the monitor is rotated in the arrow IIIa direction in FIG. 13A;

FIG. 14A is a schematic diagram showing that the monitor in the observation system according to the fifth embodiment is observed from the arrow γ direction shown in FIG. 10, a solid line shows the parallel state of the monitor with respect to the floor surface, and a broken line shows a state in which the monitor is rotated in an arrow IIIb direction;

FIG. 14B is a schematic diagram of the insertion section of the endoscope in the observation system according to the fifth embodiment, a solid line shows a state in which the insertion section of the endoscope crosses the floor surface at right angles, and a broken line shows a curved state of the curved portion of the insertion section of the endoscope, curved in conjunction at a time when the monitor is rotated in the arrow IIIb direction in FIG. 14A;

DETAILED DESCRIPTION OF THE INVENTION

Preferable embodiments of the present invention will be described hereinafter with reference to the drawings.

First, a first embodiment will be described with reference to FIGS. 1 to 3.

Figure 1:
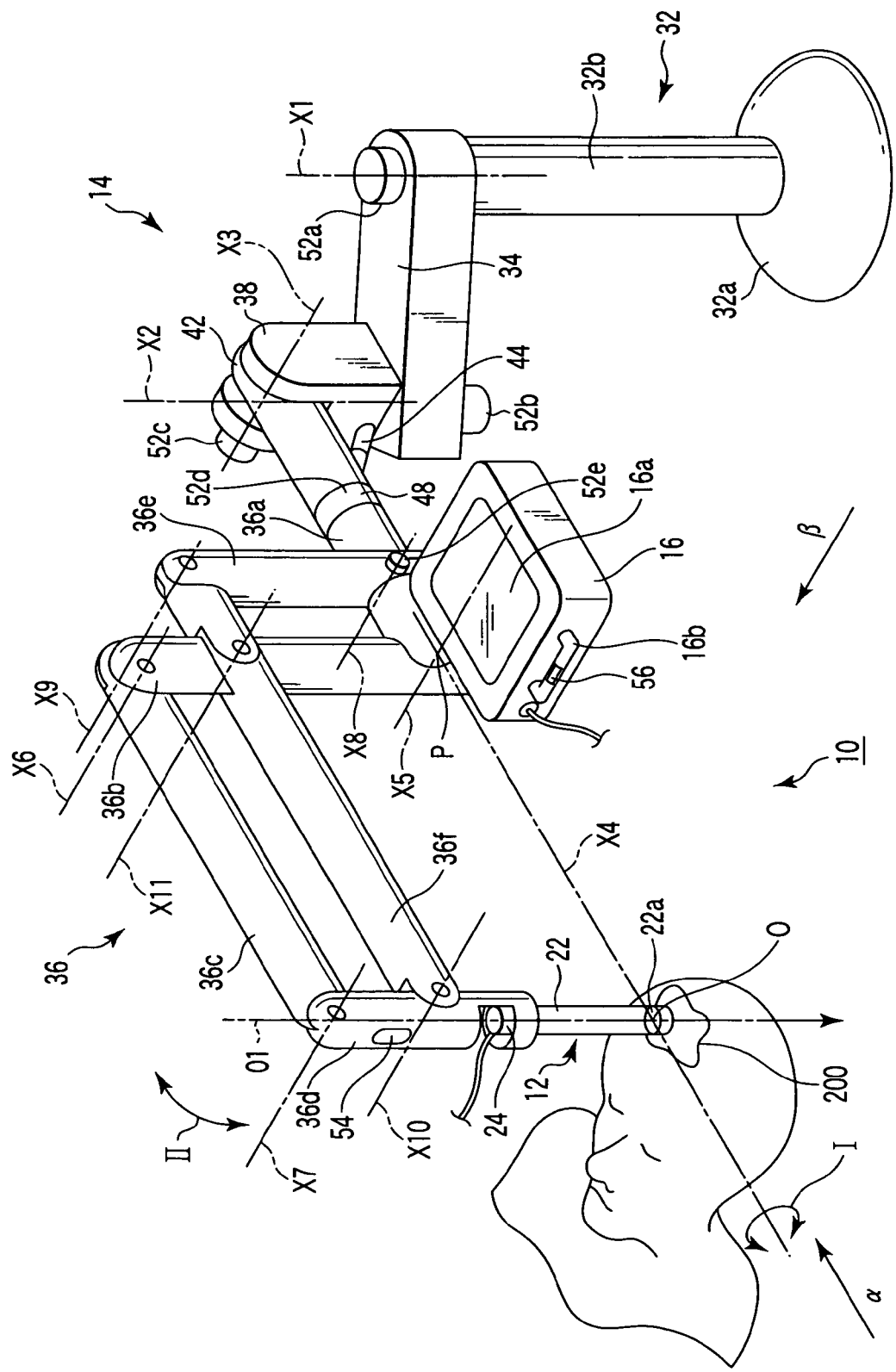
FIG. 1 is a perspective view showing a schematic configuration of an observation system according to a first embodiment of the present invention.

As shown in FIG. 1, an observation system 10 according to the embodiment includes an endoscope (observation device) 12, a first holding device 14, and a monitor 16 to reflect an operative part whose image is picked up by the endoscope 12. The endoscope 12 and monitor 16 are movably and fixably disposed by the holding device 14 in such a manner that they are moved to a desired position and held (fixed) in the desired position.

The endoscope 12 includes an elongated hard insertion section 22 to be inserted in a body cavity. That is, a so-called rigidscope is used in the endoscope 12 in order to prevent deformation during insertion into the body cavity. An objective lens 22a for guiding an optical image into a proximal end portion (upper end portion) of the insertion section 22 is disposed in a distal portion (lower end portion) of the insertion section 22. In the proximal end portion of the insertion section 22, a TV camera 24 which is an image pickup device for picking up an optical image incident upon the insertion section 22 is optically connected to the insertion section 22 and disposed. The TV camera 24 is electrically connected to the monitor 16 constituting a display device via a control unit (not shown).

The holding device 14 includes a first support mechanism 32, a first revolving arm (horizontal moving mechanism) 34, and a first parallel link mechanism (equivalent movement mechanism) 36. The first parallel link mechanism 36 includes two parallel links connected to each other. The support mechanism 32 includes a first base 32a fixed, for example, to a floor, bed or the like, and a first base arm 32b whose lower end portion is supported, so that the arm is disposed upwards, for example, in a vertical direction with respect to the base 32a.

One end portion of the revolving arm 34 is supported by the upper end portion of the base arm 32b to extend in a horizontal direction. This revolving arm 34 is rotatable around a first rotation axis X1 extending in the vertical direction in the upper end portion of the base arm 32b. A first bearing portion 38 is disposed in the other end portion of the revolving arm 34. The first bearing portion 38 is rotatable around a second rotation axis X2 which extends in the vertical direction in the other end portion of the revolving arm 34.

In the first bearing portion 38, one end portion of a first elevator arm (vertical moving mechanism, vertical moving mechanism) 42 is supported. This elevator arm 42 is rotatable around a third rotation axis X3 which extends in the horizontal direction in the first bearing portion 38. The third rotation axis X3 has a direction crossing an axial direction of the elevator arm 42 at right angles.

A first gas spring 44 is extended between the elevator arm 42 and the first bearing portion 38. This gas spring 44 offsets a moment generated by weights of the parallel link mechanism 36, endoscope 12, TV camera 24, and monitor 16.

A second bearing portion 48 is disposed in the other end portion of the elevator arm 42. The second bearing portion 48 is rotatable around a fourth rotation axis X4 which extends in the axial direction of the elevator arm 42 on the other end portion of the elevator arm 42. The first parallel link mechanism 36 is disposed in the second bearing portion 48 of the other end portion of the elevator arm 42. The parallel link mechanism 36 includes first to sixth arms 36a to 36f.

One end portion of the first arm 36a is supported by the second bearing portion 48. The axial direction of the first arm 36a matches the fourth rotation axis X4. Therefore, the first arm 36a is rotatable around the fourth rotation axis X4 by the second bearing portion 48.

The lower end portion of the second arm 36b is supported to be rotatable around a fifth rotation axis X5 in the other end portion of the first arm 36a. The upper end portion of the second arm 36b is supported to be rotatable around a sixth rotation axis X6 in one end portion of the third arm 36c. The other end portion of the third arm 36c is supported to be rotatable around a seventh rotation axis X7 in the upper end portion of the fourth arm 36d.

The lower end portion of the fifth arm 36e is supported to be rotatable around an eighth rotation axis X8 between one end portion and the other end portion of the first arm 36a. The fifth arm 36e is parallel to the second arm 36b. The upper end portion of the fifth arm 36e is supported to be rotatable around a ninth rotation axis X9 in one end portion of the sixth arm 36f. The sixth arm 36f is parallel to the third arm 36c. The other end portion of the sixth arm 36f is supported to be rotatable around a tenth rotation axis X10 in the fourth arm 36d. The sixth arm 36f and second arm 36b are supported to be rotatable around an eleventh rotation axis X11. A first parallel link includes the first arm 36a, second arm 36b, fifth arm 36e, and sixth arm 36f. A second parallel link includes the second arm 36b, third arm 36c, fourth arm 36d, and sixth arm 36f. Therefore, the second arm 36b and sixth arm 36f are disposed in common with the first and second parallel links. The parallel link mechanism 36 is formed in this manner.

The upper end portion of the insertion section 22 of the endoscope 12 is supported by the lower end portion of the fourth arm (first holding section) 36d. The objective lens 22a of the lower end portion of the insertion section 22 is disposed on the fourth rotation axis X4. That is, the endoscope 12 is attached to the fourth arm 36d in such a manner that the objective lens 22a of the distal portion of the insertion section 22 of the endoscope 12 matches a point O on the fourth rotation axis X4. A longitudinal axis O1 of the fourth arm 36d matches the longitudinal axis of the insertion section 22 of the endoscope 12, and also matches an observation direction axis of the endoscope 12.

The monitor 16 is attached to the fifth rotation axis (second holding section) X5 of the lower end portion of the fifth arm 36e. A display surface 16a of the monitor 16 is attached to the observation direction axis (longitudinal axis) O1 of the endoscope 12 in a vertical state.

A first electromagnetic brake 52a is disposed on a connecting portion between the base arm 32b and revolving arm 34 of the support mechanism 32. The electromagnetic brake 52a is switchable to a braking-on state in which the rotation of the revolving arm 34 around the first rotation axis X1 is electrically controlled and a braking-off state in which the rotation around the first rotation axis X1 is allowed.

A second electromagnetic brake 52b is disposed on the connecting portion between the revolving arm 34 and the first bearing portion 38. The second electromagnetic brake 52b is switchable to a braking-on state in which the rotation of the first bearing portion 38 around the second rotation axis X2 is electrically controlled and a braking-off state in which the rotation around the second rotation axis X2 is allowed.

A third electromagnetic brake 52c is disposed on the connecting portion between the first bearing portion 38 and the elevator arm 42. The third electromagnetic brake 52c is switchable to a braking-on state in which the rotation of the elevator arm 42 around the third rotation axis X3 is electrically controlled and a braking-off state in which the rotation around the third rotation axis X3 is allowed.

A fourth electromagnetic brake 52d is disposed on the connecting portion between the elevator arm 42 and the first arm 36a of the parallel link mechanism 36. The fourth electromagnetic brake 52d is switchable to a braking-on state in which the rotation of the first arm 36a around the fourth rotation axis X4 is electrically controlled and a braking-off state in which the rotation around the fourth rotation axis X4 is allowed.

A fifth electromagnetic brake 52e is disposed on the connecting portion between the first arm 36a and the fifth arm 36e. The fifth electromagnetic brake 52e is switchable to a braking-on state in which the rotation of the fifth arm 36e around the eighth rotation axis X8 is electrically controlled and a braking-off state in which the rotation around the eighth rotation axis X8 is allowed.

The first to fifth electromagnetic brakes 52a to 52e are connected to a first brake switch 54 disposed on the fourth arm 36d. In response to a switching operation (pressing operation) of the first brake switch 54, the first to fifth electromagnetic brakes 52a to 52e operate to selectively switch the respective arms 34, 42, the first and second bearing portions 38, 48, and the parallel link mechanism 36 to the braking-on state and the braking-off state.

The fourth and fifth electromagnetic brakes 52d, 52e are connected to a second brake switch 56 disposed in a grip 16b of the monitor 16. In response to the switching operation of the second brake switch 56, the fourth and fifth electromagnetic brakes 52d, 52e operate to selectively switch the parallel link mechanism 36 to the braking-on state and the braking-off state.

Next, a function of the observation system 10 according to the present embodiment will be described. Here, a function of disposing the distal portion of the insertion section 22 of the endoscope 12 in a desired position in a patient's operative part 200 and in a desired direction.

The operator grasps the fourth arm 36d while pressing the first brake switch 54. The first to fifth electromagnetic brakes 52a to 52e are switched to the braking-off state from the braking-on state all together. In this state, the operator rotates and deforms the holding device 14 of the observation system 10 around the first to eleventh rotation axes X1 to X11.

When the controls of the first and second electromagnetic brakes 52a, 52b are released, the revolving arm 34 and first bearing portion 38 are rotatable centering on the first and second rotation axes X1, X2. Therefore, the operator can adjust a horizontal direction position of the endoscope 12. When the control of the third electromagnetic brake 52c is released, the elevator arm 42 is rotatable centering on the third rotation axis X3. Therefore, the operator can adjust a vertical direction position of the endoscope 12.

When the control of the fourth electromagnetic brake 52d is released, the parallel link mechanism 36 is entirely rotatable centering on the fourth rotation axis X4 by the first arm 36a. Therefore, the operator can incline the endoscope 12 in an arrow direction shown by a symbol I in FIG. 1 (symbol Ia in FIG. 2A, symbol Ib in FIG. 2B).

Figure 2A:
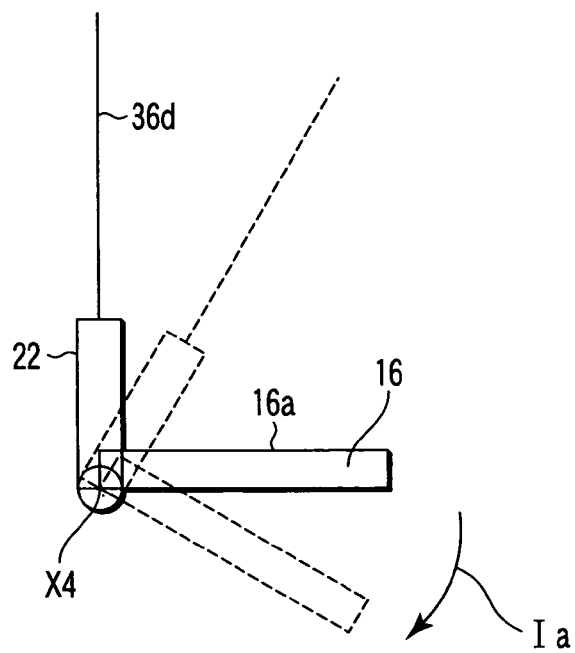
FIG. 2A is a schematic diagram showing that a positional relation between an endoscope and a monitor of the observation system according to the first embodiment is observed from an arrow α direction in FIG. 1, a solid line shows a state in which the monitor is parallel to a floor surface and an insertion section of the endoscope crosses the floor surface at right angles, and a broken line shows a state in which the monitor and the insertion section of the endoscope are rotated around a rotation axis X4 which is a support point in an arrow Ia direction.

At this time, a force is applied to the fourth arm 36d in order to incline the insertion section 22 of the endoscope 12 in a state shown by a broken line with respect to the position shown by a solid line in FIG. 2A. The insertion section 22 of the endoscope 12 rotates in the arrow direction shown by the symbol Ia in FIG. 2A centering on the fourth rotation axis X4 of the first arm 36a (see FIG. 1). Since the monitor 16 is attached to the fifth rotation axis X5, the display surface 16a of the monitor 16 maintains the vertical state with respect to an observation direction axis (longitudinal axis) O1 of the endoscope 12, and is inclined in an arrow Ia direction by the fourth rotation axis X4.

Since the distal portion of the insertion section 22 of the endoscope 12 is constantly disposed on the fourth rotation axis X4, the position of the distal portion of the insertion section 22 does not fluctuate even with the rotation of the first arm 36a around the fourth rotation axis X4.

Figure 2B:
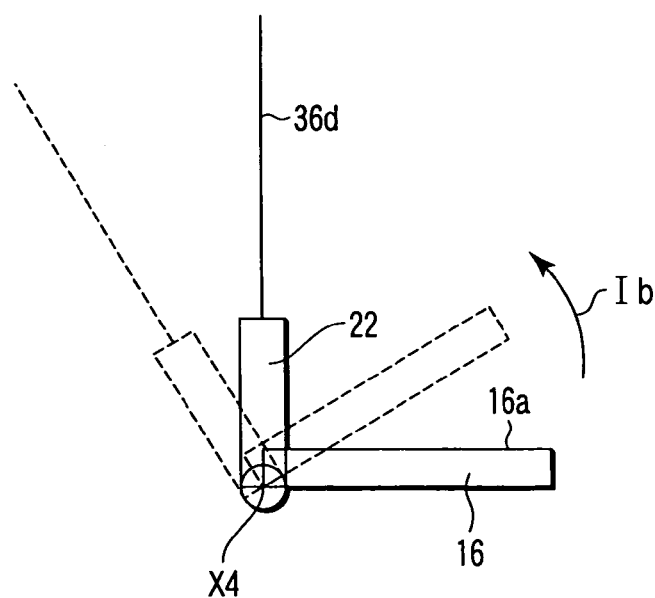
FIG. 2B is a schematic diagram showing that the positional relation between the endoscope and the monitor of the observation system according to the first embodiment is observed from the arrow α direction in FIG. 1, a solid line shows a state in which the monitor is parallel to the floor surface and the insertion section of the endoscope crosses the floor surface at right angles, and a broken line shows a state in which the monitor is rotated around the rotation axis X4 which is the support point in an arrow Ib direction.

A force is applied to the fourth arm 36d to incline the insertion section 22 of the endoscope 12 in a state shown by a broken line with respect to the position shown by a solid line in FIG. 2B. The first arm 36a (see FIG. 1) rotates centering on the fourth rotation axis X4, and the insertion section 22 of the endoscope 12 rotates in the arrow direction shown by the symbol Ib in FIG. 2B. Since the monitor 16 is attached to the fifth rotation axis X5, the display surface 16a of the monitor 16 maintains the vertical state with respect to the observation direction axis (longitudinal axis) O1 of the endoscope 12, and is inclined in the arrow Ib direction by the fourth rotation axis X4.

As shown in FIG. 1, when the control of the fifth electromagnetic brake 52e is released, the parallel link mechanism 36 is rotatable centering on the fifth to eleventh rotation axes X5 to X11 of the second to sixth arms 36b to 36f. Therefore, the operator can incline the endoscope 12 in the arrow direction shown by a symbol II in FIG. 1 (symbol IIa in FIG. 3A, symbol IIb in FIG. 3B).

Figure 3A:
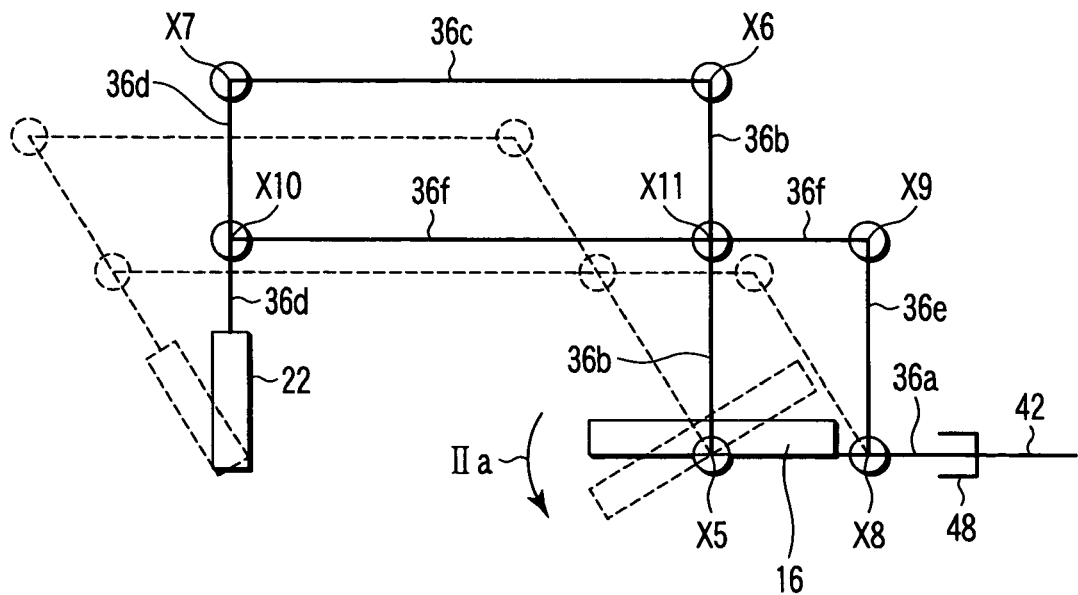
FIG. 3A is a schematic diagram showing that an operation of a parallel link mechanism of the observation system according to the first embodiment is observed from an arrow β direction in FIG. 1, a solid line shows a state in which the monitor is parallel to the floor surface and the insertion section of the endoscope crosses the floor surface at right angles, and a broken line shows a state in which the parallel link mechanism is rotated in an arrow IIa direction.

At this time, a force is applied to the fourth arm 36d to incline the endoscope 12 in the state shown by a broken line with respect to the position shown by a solid line in FIG. 3A. The fourth arm 36d rotates centering on the seventh and tenth rotation axes X7, X10 in the arrow direction shown by a symbol IIa in FIG. 3A. The third and sixth arms 36c, 36f hold parallel states, and move on the left side in FIG. 3A with the rotations of the seventh and tenth rotation axes X7, X10. The second arm 36b moves centering on the fifth rotation axis X5 on the left side in FIG. 3A. That is, the sixth and eleventh rotation axes X6 to X11 move centering on the fifth rotation axis X5 on the left side in FIG. 3A. The fifth arm 36e moves centering on the eighth rotation axis X8 on the left side in FIG. 3A. That is, the ninth rotation axis X9 moves centering on the eighth rotation axis X8 on the left side in FIG. 3A. When the parallel link mechanism 36 rotates and is deformed centering on the fifth to eleventh rotation axes X5 to X11 in this manner, the endoscope 12 is inclined in a state shown by a broken line with respect to the position shown by a solid line in FIG. 3A.

Figure 3B:
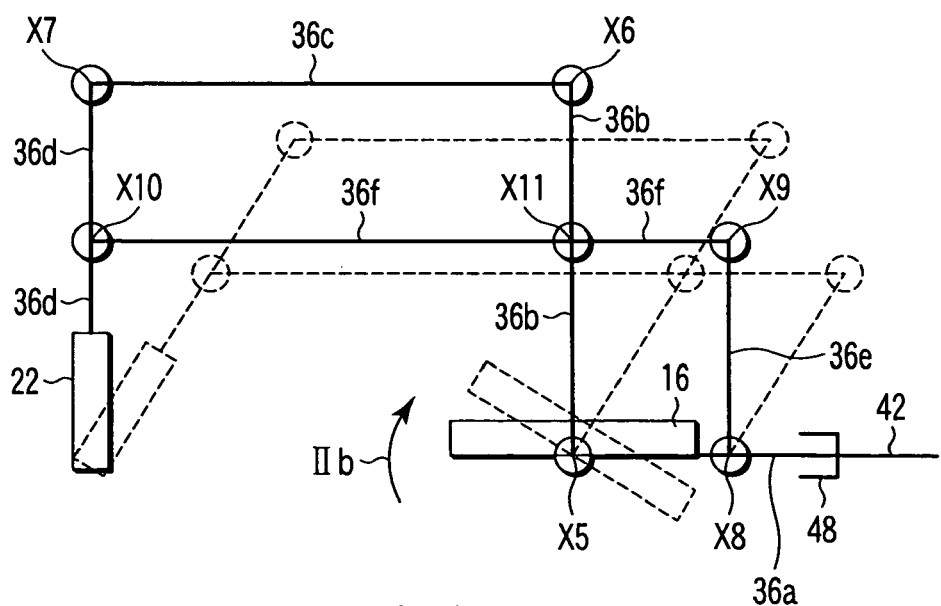
FIG. 3B is a schematic diagram showing that the operation of the parallel link mechanism of the observation system according to the first embodiment is observed from the arrow β direction in FIG. 1, a solid line shows a state in which the monitor is parallel to the floor surface and the insertion section of the endoscope crosses the floor surface at right angles, and a broken line shows a state in which the parallel link mechanism is rotated in an arrow IIb direction.

A force is applied to the fourth arm 36d to incline the endoscope 12 in the state shown by a broken line with respect to the position shown by a solid line in FIG. 3B. The fourth arm 36d rotates centering on the seventh and tenth rotation axes X7, X10 in an arrow direction shown by a symbol IIb in FIG. 3B. The third and sixth arms 36c, 36f maintain the parallel state while moving on the right side in FIG. 3B with the rotations of the seventh and tenth rotation axes X7, X10. The second arm 36b moves centering on the fifth rotation axis X5 on the right side in FIG. 3B. That is, the sixth and eleventh rotation axes X6, X11 move centering on the fifth rotation axis X5 on the right side in FIG. 3B. The fifth arm 36e moves centering on the eighth rotation axis X8 on the right side in FIG. 3B. That is, the ninth rotation axis X9 moves centering on the eighth rotation axis X8 on the right side in FIG. 3B. When the parallel link mechanism 36 rotates and is deformed centering on the fifth to eleventh rotation axes X5 to X11 in this manner, the endoscope 12 is inclined in a state shown by a broken line with respect to the position shown by a solid line in FIG. 3B.

By a combination of the movements of the support mechanism 32 of the holding device 14, the revolving arm 34, the first and second bearing portions 38, 48, the elevator arm 42, and the parallel link mechanism 36, the operator disposes the distal portion of the insertion section 22 of the endoscope 12 in the desired position in the patient's operative part 200 and in the desired direction. The operator can grasp and operate the fourth arm 36d to move the endoscope 12 to three-dimensional free position and angle.

When the fourth arm 36d is inclined to incline the endoscope 12 in an arrow I (Ia, Ib) direction, the whole parallel link mechanism 36 is inclined centering on the fourth rotation axis X4. Therefore, the monitor 16 is inclined. The display surface 16a of the monitor 16 is set to the vertical state with respect to the observation direction axis O1 of the endoscope 12.

When the fourth arm 36d is inclined to incline the endoscope 12 in an arrow II (IIa, IIb) direction by the deformation of the parallel link mechanism 36, the second arm 36b is parallel to the fourth arm 36d. Therefore, the monitor 16 rotates centering on the fifth rotation axis X5 in synchronization with the second arm 36b. Therefore, the display surface 16a of the monitor 16 is set to the vertical state with respect to the observation direction axis O1 of the endoscope 12. The parallel link mechanism 36 includes two parallelogram links: a first parallelogram link holding the monitor 16 and including the second, third, fourth, and sixth arms 36b, 36c, 36d, 36f; and a second parallelogram link holding the endoscope 12 and including the first, second, fifth, and sixth arms 36a, 36b, 36e, 36f. Therefore, the parallelogram link is an equivalent movement mechanism. A point O and an intersection P between the fourth and fifth rotation axes X4, X5 are equivalently rotated in synchronization with the deformation of the parallel link mechanism 36. That is, the points O, P perform equivalent movement.

When the distal portion of the insertion section 22 of the endoscope 12 is disposed in the desired position and direction, the operator releases the first brake switch 54. The first to fifth electromagnetic brakes 52a to 52e are switched to the braking-on state from the braking-off state all together or with a slight time difference. The distal portion of the insertion section 22 of the endoscope 12 is disposed and fixed in the desired position and direction in this manner.

To move only the parallel link mechanism 36 and monitor 16 in a state in which the revolving arm 34 and first bearing portion 38 are fixed, the operator grasps the grip 16b of the monitor 16 while pressing the second brake switch 56. The fourth and fifth electromagnetic brakes 52d, 52e are switched to the braking-off state from the braking-on state all together. In this state, the operator rotates and deforms the parallel link mechanism 36 of the holding device 14 of the observation system 10 around the fourth to eleventh rotation axes X4 to X11 in the arrow I, II direction in FIG. 1 to move the endoscope 12 to the desired position and in the desired direction. That is, the operator grasps the grip 16b of the monitor 16 while moving the parallel link mechanism 36 to dispose the endoscope 12 in the desired position and direction.

When the distal portion of the insertion section 22 of the endoscope 12 is disposed in the desired position and direction, the operator releases hands off the second brake switch 56. The fourth and fifth electromagnetic brakes 52d, 52e are switched to the braking-off state from the braking-on state all together or with a slight time difference. The distal portion of the insertion section 22 of the endoscope 12 is disposed and fixed in the desired position and direction in this manner.

As described above, according to the embodiment, the following can be said.

The objective lens 22a of the endoscope 12 of the observation system 10 is disposed in the point O which is an intersection between the fourth rotation axis X4 of the parallel link mechanism 36 and the observation direction axis O1. The monitor 16 is disposed on the fifth rotation axis X5 including an immobile point of the parallel link mechanism 36, and is moved in synchronization with the deformation of the parallel link mechanism 36. Therefore, movement amounts of the endoscope 12 and monitor 16 can be set to be minimum. The view field direction of the operative part 200 to be observed by the endoscope 12 can be easily adjusted, and the monitor 16 can be prevented from interfering with the parallel link mechanism 36.

The observation system 10 is constituted such that the display surface 16a of the monitor 16 displaying video obtained by the use of the endoscope 12 constantly keeps its vertical state even when the observation direction axis O1 changes. Therefore, when the moving direction of the observation direction axis O1 becomes identical to that of an optical image in the display surface 16a, the operator can easily grasp the observation direction axis O1 of the endoscope 12 in the body, which cannot be directly confirmed with eyes.

The grip 16b of the monitor 16 which displays the video of the endoscope 12 is grasped, the second brake switch 56 is pressed to switch the fourth and fifth electromagnetic brakes 52d, 52e to the braking-off state, and the endoscope 12 is moved. When the observation direction axis O1 of the endoscope 12 is changed in this manner, the operator can perform the treatment and diagnosis with natural sense.

Next, a second embodiment will be described with reference to FIGS. 4 and 5. This embodiment is a modification of the first embodiment, the same members as those described in the first embodiment are denoted with the same reference numerals, and detailed description is omitted.

Figure 4:
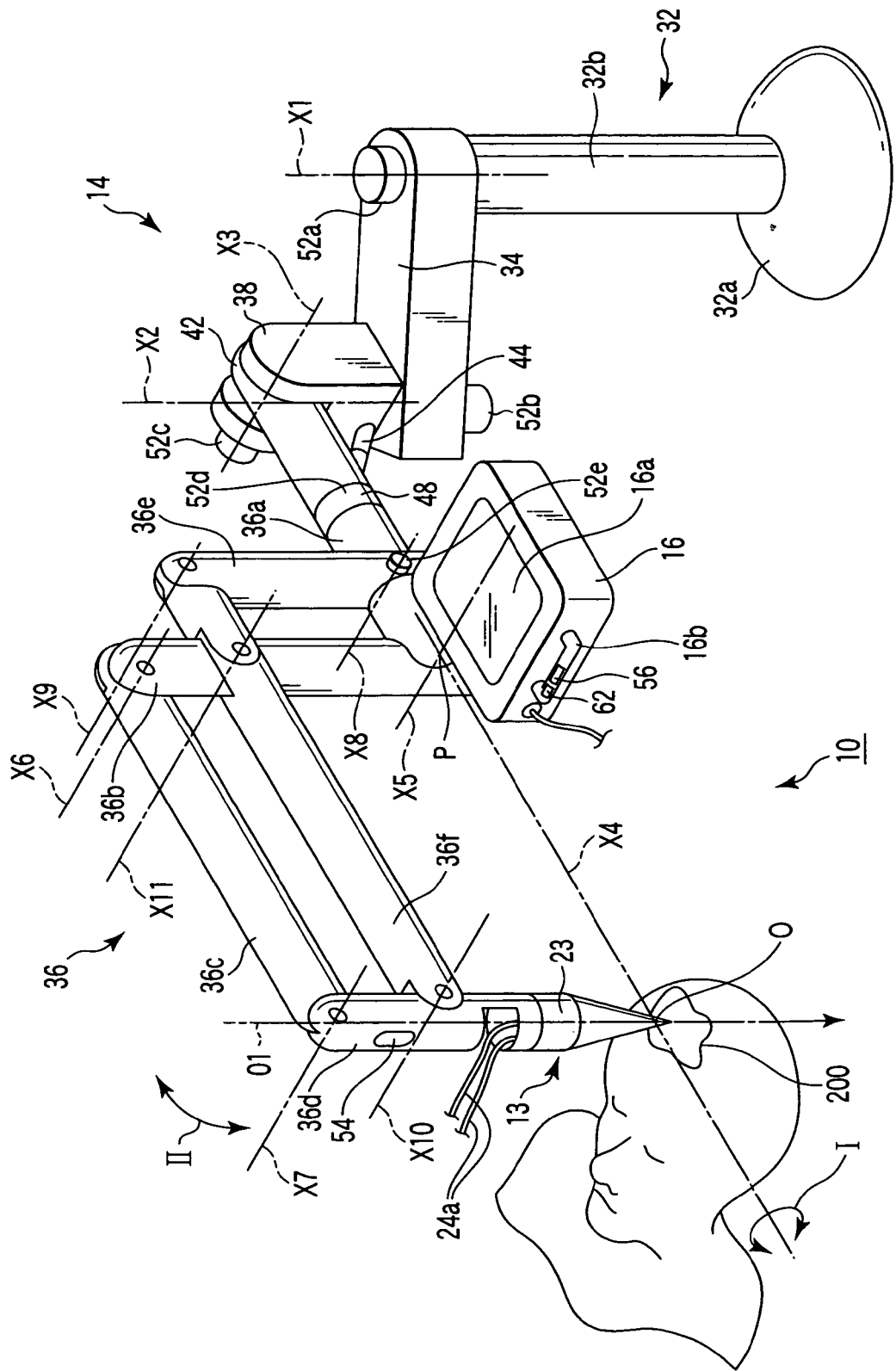
FIG. 4 is a perspective view showing a schematic configuration of the observation system according to a second embodiment of the present invention.
Figure 5:
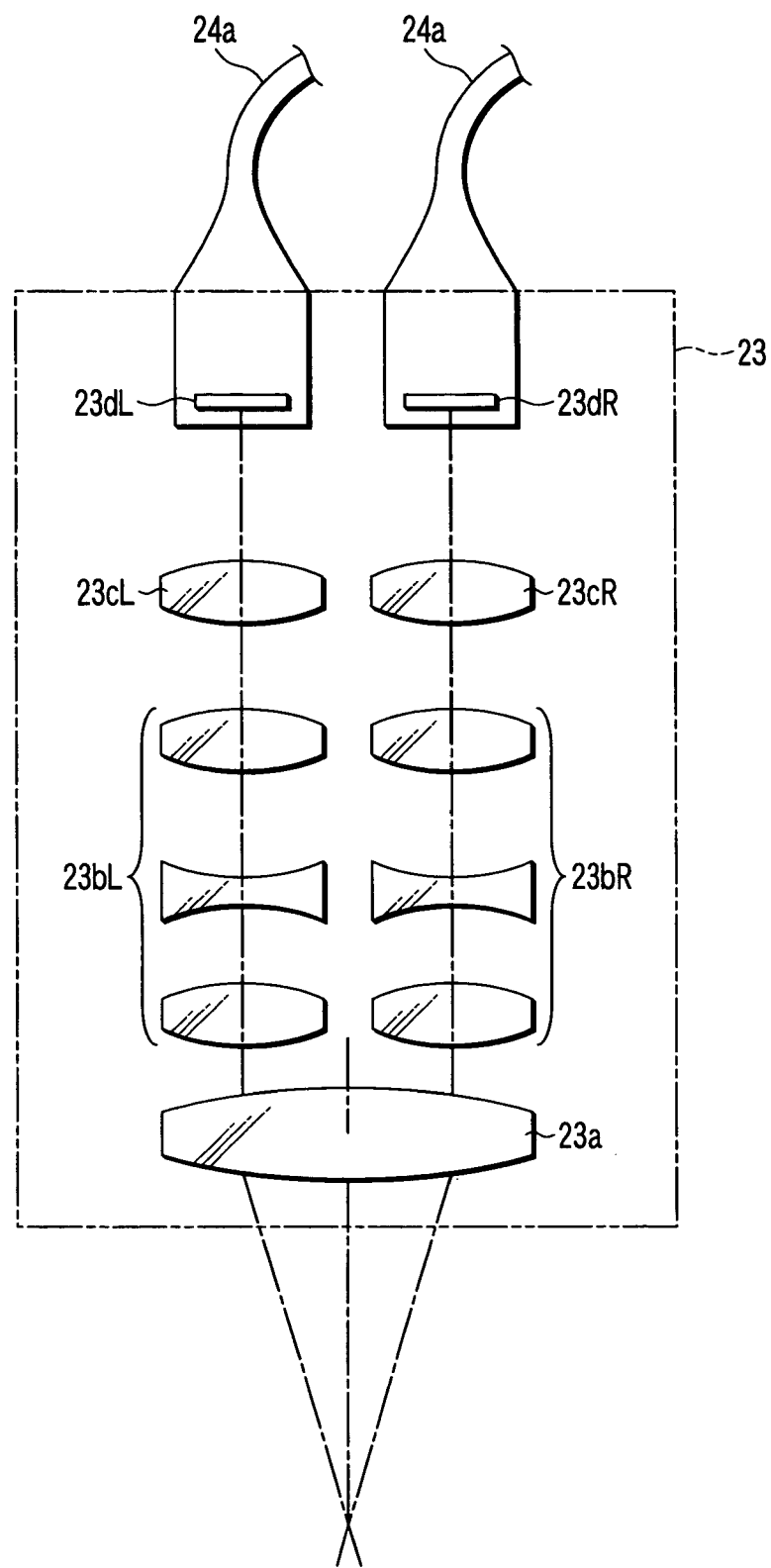
FIG. 5 is a schematic diagram showing an inner structure of a microscope body of an electronic image microscope shown in FIG. 4 in the observation system according to the second embodiment.

As shown in FIG. 4, in the observation system 10 according to the present embodiment, a microscope body 23 of an electronic image microscope (observation device) 13 is disposed instead of the endoscope 12. As shown in FIG. 5, the microscope body 23 includes an optical objective system 23a, a pair of optical variable magnification systems 23bR, 23bL in which a plurality of lenses are combined, a pair of image forming lenses 23cR, 23cL, and a pair of image pickup devices 23dR, 23dL. Cables 24a extend from the pair of image pickup devices 23dR, 23dL. These cables 24a are electrically connected to the monitor 16 shown in FIG. 4 via a control unit (not shown). That is, the image pickup device 23dR for the right eye and the image pickup device 23dL for the left eye are electrically connected to the monitor (stereoscopic display device) 16.

Therefore, a pair of optical images picked up by these image pickup device 23dR for the right eye and the image pickup device 23dL for the left eye are displayed in the display surface 16a of the monitor 16 and stereoscopically observed by the operator. A single lens in which only one optical objective system, optical variable magnification system, image forming lens, and image pickup device are disposed may also be constituted.

Each of the optical variable magnification systems 23bR, 23bL includes a frame (not shown) which moves a part of the lens along the optical axis O1 of the microscope body 23. A motor (not shown) is attached to the frame. Therefore, when the motor is driven, the frame moves along the optical axis O1, and distances between the lenses change to change an observation magnification. A variable magnification driving switch 62 of the motor is disposed on the grip 16b of the monitor 16. Therefore, when the operator grasps the grip 16b of the monitor 16 while pressing the variable magnification driving switch 62, the magnification of the image picked up by the image pickup devices 23dR, 23dL is changed.

Next, a function of the observation system 10 according to the embodiment will be described.

To observe an operation field, the operator presses the first brake switch 54 to move the microscope body 23 of the electronic image microscope 13 to the desired position. The pressed first brake switch 54 is released to fix the microscope body 23 of the electronic image microscope 13 in the desired position. In this case, the monitor 16 moves together with the microscope body 23 of the electronic image microscope 13 in the same manner as in the first embodiment using the endoscope 12 (see FIG. 1). The display surface 16a of the monitor 16 is constantly kept in the vertical state with respect to the optical axis O1 of the microscope body 23 of the electronic image microscope 13.

Next, the operator presses the variable magnification driving switch 62 disposed on the grip 16b of the monitor 16 to enlarge and display the operative part, and performs fine treatment with respect to the operative part. The second brake switch 56 is pressed to treat the peripheral portion of the operative part. At this time, not only the fourth and fifth electromagnetic brakes 52d, 52e are released but also all of the first to fifth electromagnetic brakes 52a to 52e are released in the same manner as in the pressed first brake switch 54. Therefore, while seeing the display surface 16a of the monitor 16, the monitor 16 is held in a position to be observed, and the microscope body 23 of the electronic image microscope 13 is moved.

At this time, the microscope body 23 of the electronic image microscope 13 moves in conjunction with the monitor 16, and the view field of the microscope body 23 of the electronic image microscope 13 also moves. In this case, the optical axis O1 of the microscope body 23 of the electronic image microscope 13 and the display surface 16a of the monitor 16 are constantly kept in the vertical state. Therefore, the direction of the operative part observed by the stereoscopic optical system of the microscope body 23 is easily recognized by the operator.

As described above, according to the present embodiment, the following can be said in addition to the first embodiment.

With the use of the electronic image microscope 13, visual observation of the distal portion of the insertion section 22 of the endoscope 12 inserted into the body is not inhibited as in the endoscope 12 (see FIG. 1). Since the microscope body 23 and the monitor 16 can keep a specific positional relation, the operator can easily grasp the angle and direction of the operative part observed using the electronic image microscope 13 when seeing the display surface 16a of the monitor 16.

Moreover, the positional relation between the microscope body 23 of the electronic image microscope 13 and the display surface 16a of the monitor 16 is kept in a specific state. Therefore, during insertion of hand, treatment equipment or the like into the operative part, when the hand or the like is actually inserted into the operative part from the left, the display surface 16a does not display as if the hand or the like were inserted, for example, from above or below. When the hand or the like is inserted from the left, the display surface 16a also displays that it is inserted from the left. Therefore, the operator can perform the surgical operation with more natural sense.

Next, a third embodiment will be described with reference to FIGS. 6 and 7. The present embodiment is a modification of the first embodiment, the same members as those described in the first embodiment are denoted with the same reference numerals, and the detailed description is omitted.

Figure 6:
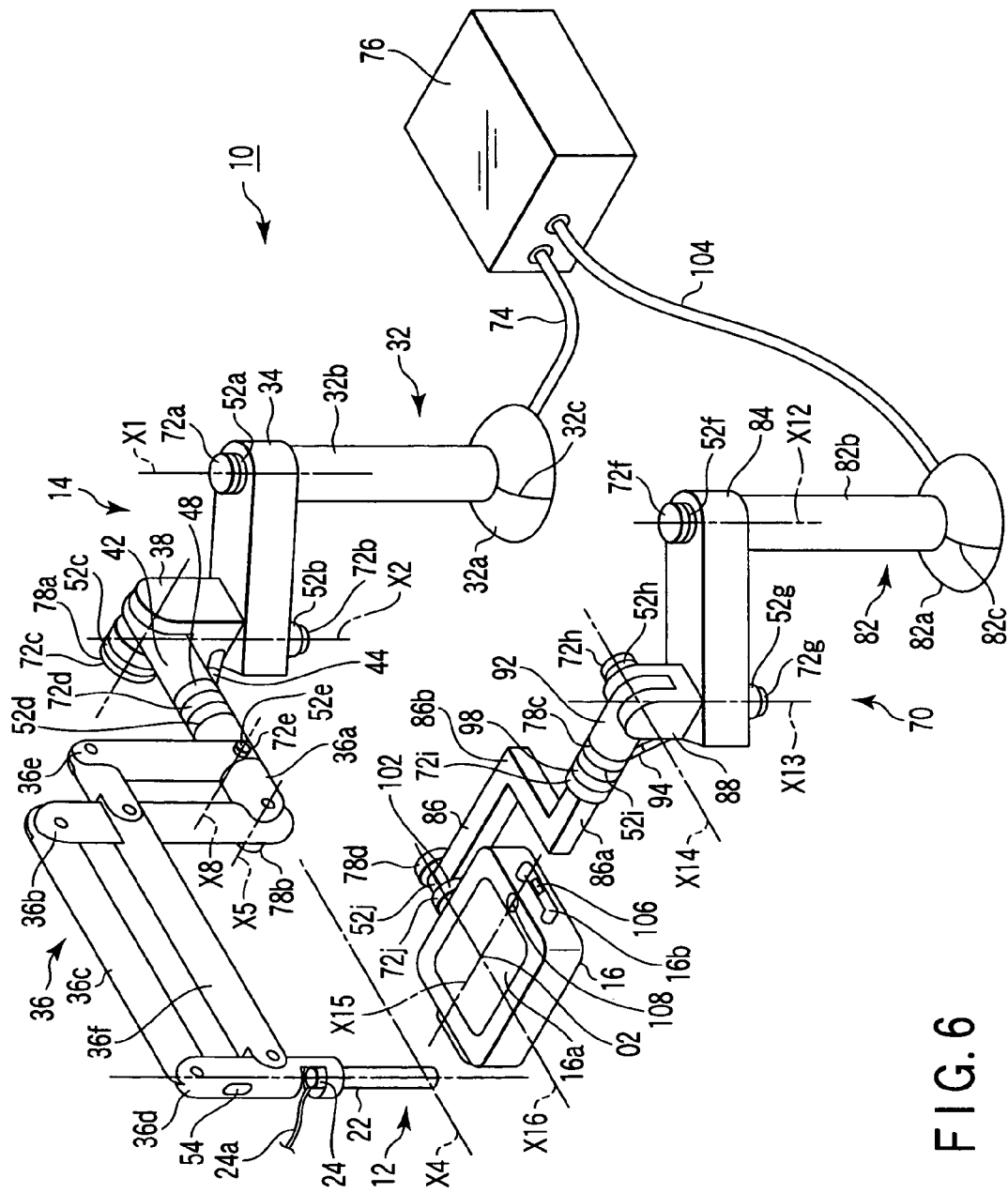
FIG. 6 is a perspective view showing a schematic configuration of the observation system according to a third embodiment of the present invention.

As shown in FIG. 6, in the embodiment, unlike the first embodiment, the monitor 16 is detached from the fifth rotation axis X5 of the first holding device 14. Instead, the observation system 10 newly includes a second holding device (second movable member) 70 which holds the monitor 16.

The constitution of the first holding device (first movable member) 14 which holds the endoscope 12 will be described. Further in addition to the first holding device 14 described in the first embodiment, an index for calibration 32c is disposed in the first base 32a of the first support mechanism 32.

A first encoder (posture detection mechanism) 72a is disposed on the connecting portion between the upper end portion of the first base arm 32b of the support mechanism 32 and one end portion of the first revolving arm 34. This first encoder 72a is capable of detecting a rotation angle of the revolving arm 34 around the first rotation axis X1 with respect to the base arm 32b.

A second encoder 72b is disposed on the connecting portion of the first revolving arm 34 with the first bearing portion 38. The second encoder 72b is capable of detecting the rotation angle of the first bearing portion 38 around the second rotation axis X2 with respect to the revolving arm 34.

A third encoder 72c is disposed on the connecting portion of the first bearing portion 38 with one end portion of the elevator arm 42. The third encoder 72c is capable of detecting the rotation angle of the elevator arm 42 around the third rotation axis X3 with respect to the first bearing portion 38.

A fourth encoder 72d is disposed on the connecting portion of the other end portion of the elevator arm 42 with the first arm 36a. The fourth encoder 72d is capable of detecting the rotation angle of the first arm 36a around the fourth rotation axis X4 with respect to the elevator arm 42.

A fifth encoder 72e is disposed on the connecting portion of the first arm 36a with the fifth arm 36e. The fifth encoder 72e is capable of detecting the rotation angle of the fifth arm 36e around the eighth rotation axis X8 with respect to the first arm 36a. These first to fifth encoders 72a to 72e are electrically connected to a controller 76 via a cable 74. The controller 76 is electrically connected to the TV camera 24 via the cable 24a.

A first motor 78a is disposed on the second bearing portion 48 of the connecting portion of the other end portion of the elevator arm 42 with one end portion of the first arm 36a. The first motor 78a constitutes posture adjustment mechanism for rotating the first arm 36a centering on the fourth rotation axis X4 with respect to the elevator arm 42.

A second motor 78b is disposed on the connecting portion of the first arm 36a with the second arm 36b. The second motor 78b rotates the second arm 36b centering on the fifth rotation axis X5 with respect to the first arm 36a. For example, stepping motors are used in these first and second motors 78a, 78b. These first and second motors 78a, 78b are electrically connected to the controller 76 via the cable 74 in the same manner as in the first to fifth encoders 72a to 72e.

The second holding device 70 includes a second support mechanism 82, second revolving arm 84, and rotary arm (second holding section) 86. The second support mechanism 82 includes a second base 82a fixed, for example, to a floor, bed or the like, and a second base arm 82b whose lower end portion is supported with respect to the base 82*a* in such a manner that the arm is vertically disposed, for example, upwards in the vertical direction.

One end portion of the second revolving arm 84 is supported by the upper end portion of the second base arm 82*b*, and extends in the horizontal direction. The revolving arm 84 is rotatable around a twelfth rotation axis X12 which extends in the vertical direction with respect to the upper end portion of the base arm 82*b*. A third bearing portion 88 is disposed on the other end portion of the revolving arm 84. The third bearing portion 88 is rotatable around a thirteenth rotation axis X13 which extends in the vertical direction in the other end portion of the revolving arm 34.

One end portion of an elevator arm 92 is supported by the third bearing portion 88. The elevator arm 92 is rotatable around a fourteenth rotation axis X14 which extends in the horizontal direction with respect to the third bearing portion 88. The fourteenth rotation axis X14 has a direction crossing the axial direction of the elevator arm 92 at right angles.

A second gas spring 94 is extended between the elevator arm 92 and the third bearing portion 88. The gas spring 94 offsets a moment generated by the weights of the rotary arm 86 and monitor 16.

A fourth bearing portion 98 is disposed on the other end portion of the elevator arm 92. The fourth bearing portion 98 is rotatable around a fifteenth rotation axis X15 which extends in the axial direction of the elevator arm 92 in the other end portion of the elevator arm 92.

One end portion of the rotary arm 86 is supported by the fourth bearing portion 98. The axial direction of one end portion of the rotary arm 86 matches the fifteenth rotation axis X15. Therefore, the rotary arm 86 is rotatable around the fifteenth rotation axis X15 by the fourth bearing portion 98.

The rotary arm 86 includes a first bent portion 86*a* which is bent in a direction deviating with respect to the axial direction of one end portion, and a second bent portion 86*b* parallel to the axial direction of one end portion. A fifth bearing portion 102 is disposed on the other end portion of the rotary arm 86. The fifth bearing portion 102 includes a sixteenth rotation axis X16 in a direction crossing the fifteenth rotation axis X15 of the fourth bearing portion 98 at right angles in the other end portion of the rotary arm 86. The monitor 16 is supported by the fifth bearing portion 102. The fifteenth rotation axis X15 crosses the sixteenth rotation axis X16 at right angles on the same plane. The monitor 16 is attached to the other end portion of the rotary arm 86. An intersection O2 between the fifteenth and sixteenth rotation axes X15 and X16 overlaps with a middle of the display surface 16*a* of the monitor 16.

A sixth electromagnetic brake 52*f* is disposed on the connecting portion between the second base arm 82*b* of the second support mechanism 82 and the second revolving arm 84 of the second holding device 70. The sixth electromagnetic brake 52*f* is switchable to a braking-on state in which the rotation of the revolving arm 84 around the twelfth rotation axis X12 is electrically controlled and a braking-off state in which the rotation around the twelfth rotation axis X12 is allowed.

A seventh electromagnetic brake 52*g* is disposed between the second revolving arm 84 and the third bearing portion 88. The seventh electromagnetic brake 52*g* is switchable to a braking-on state in which the rotation of the third bearing portion 88 around the thirteenth rotation axis X13 is electrically controlled and a braking-off state in which the rotation around the thirteenth rotation axis X13 is allowed.

An eighth electromagnetic brake 52*h* is disposed on the connecting portion of the third bearing portion 88 with the elevator arm 92. The eighth electromagnetic brake 52*h* is switchable to a braking-on state in which the rotation of the elevator arm 92 around the fourteenth rotation axis X14 is electrically controlled and a braking-off state in which the rotation around the fourteenth rotation axis X14 is allowed.

A ninth electromagnetic brake 52*i* is disposed on the connecting portion of the elevator arm 92 with the rotary arm 86. That is, the ninth electromagnetic brake 52*i* is disposed on the fourth bearing portion 98. The ninth electromagnetic brake 52*i* is switchable to a braking-on state in which the rotation of the rotary arm 86 around the fifteenth rotation axis X15 is electrically controlled and a braking-off state in which the rotation around the fifteenth rotation axis X15 is allowed.

A tenth electromagnetic brake 52*j* is disposed on the connecting portion of the other end portion of the rotary arm 86 with the monitor 16. That is, the tenth electromagnetic brake 52*j* is disposed on the fifth bearing portion 102. The tenth electromagnetic brake 52*j* is switchable to a braking-on state in which the rotation of the monitor 16 around the sixteenth rotation axis X16 is electrically controlled and a braking-off state in which the rotation around the sixteenth rotation axis X16 is allowed. These sixth to tenth electromagnetic brakes 52*f* to 52*j* are electrically connected to the controller 76 via a cable 104.

The sixth to tenth electromagnetic brakes 52*f* to 52*j* are electrically connected to a third brake switch 106 disposed on the grip 16*b* of the monitor 16. In response to the switching operation (pressing operation) of the third brake switch 106, the sixth to tenth electromagnetic brakes 52*f* to 52*j* operate to selectively switch the respective arms 84, 92, 86, third and fourth bearing portions 88, 98, and monitor 16 to the braking-on state and the braking-off state.

The ninth and tenth electromagnetic brakes 52*i*, 52*j* are electrically connected to a fourth brake switch 108 disposed on the side portion of the display surface 16*a* of the monitor 16. In response to the switching operation of the fourth brake switch 108, the ninth and tenth electromagnetic brakes 52*i*, 52*j* operate to selectively switch the rotary arm 86 and monitor 16 to the braking-on state and braking-off state.

A sixth encoder 72*f* is disposed on the connecting portion between the upper end portion of the second base arm 82*b* of the second support mechanism 82 of the second holding device 70 and one end portion of the second revolving arm 84. The sixth encoder 72*f* is capable of detecting the rotation angle of the revolving arm 84 around the twelfth rotation axis X12 with respect to the second base arm 82*b*.

A seventh encoder 72*g* is disposed between the second revolving arm 84 and the third bearing portion 88. The seventh encoder 72*g* is capable of detecting the rotation angle of the third bearing portion 88 around the thirteenth rotation axis X13 with respect to the revolving arm 84.

An eighth encoder 72*h* is disposed on the connecting portion of the third bearing portion 88 with one end portion of the elevator arm 92. That is, the eighth encoder 72*h* is disposed on the third bearing portion 88. The eighth encoder 72*h* is capable of detecting the rotation angle of the elevator arm 92 around the fourteenth rotation axis X14 with respect to the third bearing portion 88.

A ninth encoder 72*i* is disposed on the connecting portion of the other end portion of the elevator arm 92 with the rotary arm 86. That is, the ninth encoder 72*i* is disposed on the fourth bearing portion 98. The ninth encoder 72*i* is capable of detecting the rotation angle of the rotary arm around the fifteenth rotation axis X15 with respect to the elevator arm 92.

A tenth encoder 72*j* is disposed on the connecting portion of the other end portion of the rotary arm 86 with the monitor 16. That is, the tenth encoder 72*j* is disposed on the fifth bearing portion 102. The tenth encoder 72*j* is capable of detecting the rotation angle of the monitor 16 around the sixteenth rotation axis X16 with respect to the rotary arm 86. These sixth to tenth encoders 72f to 72j are electrically connected to the controller 76 via the cable 104.

A third motor 78c is disposed on the fourth bearing portion 98 of the connecting portion of the other end portion of the elevator arm 92 with one end portion of the rotary arm 86. The third motor 78c constitutes the posture adjustment mechanism for rotating the rotary arm 86 centering on the fifteenth rotation axis X15 with respect to the elevator arm 92.

A fourth motor 78d is disposed on the fourth bearing portion 98 of the connecting portion of the rotary arm 86 with the monitor 16. The fourth motor 78d rotates the monitor 16 centering on the sixteenth rotation axis X16 with respect to the rotary arm 86. For example, the stepping motors are used in these third and fourth motors 78c, 78d. These third and fourth motors 78c, 78d are electrically connected to the controller 76 via the cable 74 in the same manner as in the sixth to tenth encoders 72f to 72j.

An index for calibration 82c is disposed on the base 82a of the second support mechanism 82 to be aligned with the index for calibration 32c of the base 32a of the holding device 14. When the second holding device 70 is set, the index 82c is disposed substantially in parallel with the index 32c of the base 32a of the holding device 14.

Figure 7:
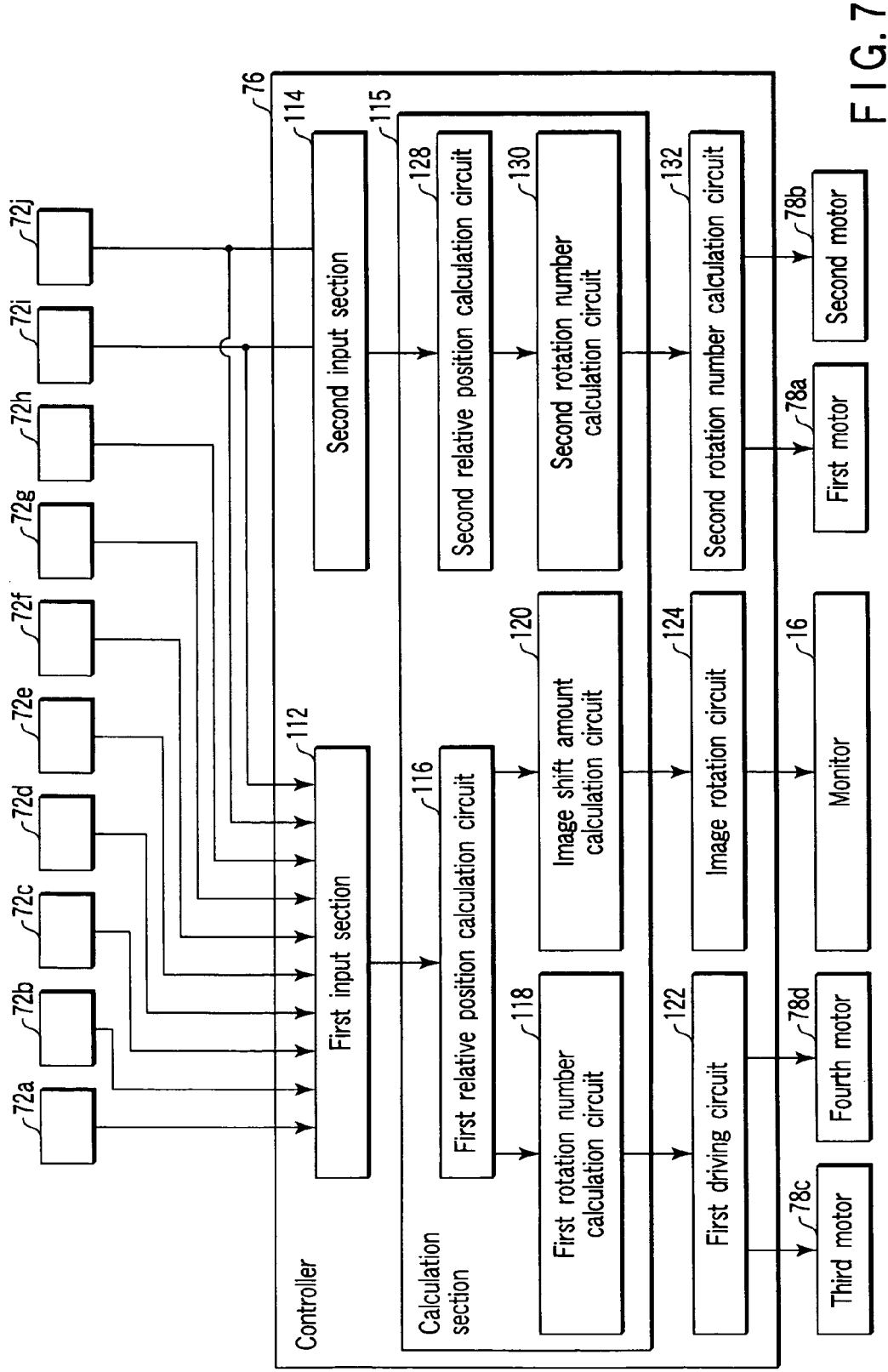
FIG. 7 is a block diagram showing a control system of the observation system according to the third embodiment.

As shown in FIG. 7, first and second input sections 112, 114 are disposed in the controller 76. The first input section 112 is connected to output ends of the first to tenth encoders 72a to 72j. The second input section 114 is connected to output ends of the ninth and tenth encoders 72i, 72j.

The output end of the first input section 112 is connected to a first relative position calculation circuit 116 of a calculation section 115 constituting calculation means. The output end of the first relative position calculation circuit 116 is connected to a first rotation number calculation circuit 118 and an image shift amount calculation circuit 120. The output end of the first rotation number calculation circuit 118 is connected to a first driving circuit 122. The first driving circuit 122 is connected to signal input ends of the third and fourth motors 78c, 78d. The output end of the image shift amount calculation circuit 120 is connected to an image rotation circuit 124. The image rotation circuit 124 is connected to the monitor 16.

The output end of the second input section 114 is connected to a second relative position calculation circuit 128. The output end of the second relative position calculation circuit 128 is connected to a second rotation number calculation circuit 130. The output end of the second rotation number calculation circuit 130 is connected to a second driving circuit 132. The output end of the second driving circuit 132 is connected to signal input ends of the first and second motors 78a, 78b.

Next, the function of the observation system 10 according to the present embodiment will be described. Here, a function of disposing the monitor 16 in a position which is easy for the operator to see, and a function of disposing the distal portion of the insertion section 22 of the endoscope 12 in the desired position in the patient's operative part 200 and in the desired direction will be described.

The function of disposing the monitor 16 in the position which is easy for the operator to see will be described.

The operator presses the third brake switch 106 in the grasped state of the grip 16b of the monitor 16. The sixth to tenth electromagnetic brakes 52f to 52j are switched to the braking-off state from the braking-on state all together. In this state, the operator rotates and deforms the second holding device 70 of the observation system 10 around the twelfth to sixteenth rotation axes X12 to X16.

When the controls of the sixth and seventh electromagnetic brakes 52f, 52g are released, the second revolving arm 84 and third bearing portion 88 are rotatable centering on the twelfth and thirteenth rotation axes X12, X13. Therefore, the operator can adjust the horizontal direction position of the monitor 16.

When the control of the eighth electromagnetic brake 52h is released, the elevator arm 92 is rotatable centering on the fourteenth rotation axis X14. Therefore, the operator can adjust the position of the monitor 16 in the vertical direction. When the control of the tenth electromagnetic brake 52j is released, the monitor 16 is rotatable centering on the sixteenth rotation axis X16. Therefore, the operator can adjust the horizontal state of the display surface 16a of the monitor 16.

When the control of the ninth electromagnetic brake 52i is released, the rotary arm 86 is rotatable centering on the fifteenth rotation axis X15 by the rotary arm 86. Therefore, the operator can incline the monitor 16 in the desired direction.

By the combination of the movements of the support mechanism 82, revolving arm 84, third and fourth bearing portions 88, 98, elevator arm 92 and rotary arm 86, the operator sets the display surface 16a of the monitor 16 in a position which is easy for the operator to see.

Next, as described in the first embodiment, the operator presses the first brake switch 54 to three-dimensionally move the endoscope 12, and disposes the distal portion of the insertion section 22 of the endoscope 12 in the desired position in the patient's operative part 200 and in the desired direction.

The first encoder 72a of the first holding device 14 detects the angle of the first revolving arm 34 with respect to the first support mechanism 32. The second encoder 72b detects the angle of the first bearing portion 38 with respect to the first revolving arm 34. The third encoder 72c detects the angle of the first elevator arm 42 with respect to the first bearing portion 38. The fourth encoder 72d detects the angle of the first arm 36a with respect to the first elevator arm 42. The fifth encoder 72e detects the angle of the fifth arm 36e with respect to the first arm 36a. The first to fifth encoders 72a to 72e output detected signals to the controller 76 via the cable 74.

Moreover, the sixth encoder 72f of the second holding device 70 detects the angle of the second revolving arm 84 with respect to the second support mechanism 82. The seventh encoder 72g detects the angle of the third bearing portion 88 with respect to the second revolving arm 84. The eighth encoder 72h detects the angle of the second elevator arm 92 with respect to the third bearing portion 88. The ninth encoder 72i detects the angle of the rotary arm 86 with respect to the second elevator arm 92. The tenth encoder 72j detects the angle of the monitor 16 with respect to the rotary arm 86. The sixth to tenth encoders 72f to 72j output the detected signals to the controller 76 via the cable 104.

Angle information detected by the first to tenth encoders 72a to 72j is input into the first input section 112 shown in FIG. 7. The first input section 112 outputs input angle information to the first relative position calculation circuit 116. The first relative position calculation circuit 116 calculates the relative position of the display surface 16a of the monitor 16 with respect to the observation direction axis O1 of the endoscope 12 using the index 32c of the first base 32a and the index 82c of the second base 82a as reference directions based on the input angle information. The first relative position calculation circuit 116 outputs relative position information to the first rotation number calculation circuit 118.

The first rotation number calculation circuit 118 calculates necessary rotation numbers of the third and fourth motors 78c, 78d required for the display surface 16a of the monitor 16 to obtain the vertical state with respect to the observation direction axis O1 of the endoscope 12 based on input relative position information. The first rotation number calculation circuit 118 outputs the necessary rotation number information to the image shift amount calculation circuit 120 and first driving circuit 122.

The first driving circuit 122 produces a driving signal based on the input necessary rotation number information to drive and control the third and fourth motors 78c, 78d. The third and fourth motors 78c, 78d rotate the rotary arm 86 and monitor 16 centering on the fifteenth and sixteenth rotation axes X15 and X16. The third and fourth motors 78c, 78d rotate until the observation direction axis O1 of the endoscope 12 obtains the vertical state with respect to the display surface 16a of the monitor 16.

The image shift amount calculation circuit 120 calculates shifts of the vertical/horizontal directions of the image picked up by the TV camera 24 and the display surface 16a of the monitor 16 to calculate an image shift amount. The image shift amount calculation circuit 120 outputs the calculated image shift amount to the image rotation circuit 124. Based on the input image shift amount, the image rotation circuit 124 produces a video signal indicating that the input video of the TV camera 24 is rotated to set a moving direction of a view field by the moving of the endoscope 12 to be the same as that on the monitor 16. The image rotation circuit 124 outputs and displays the produced video signal to the monitor 16.

To change the view field direction during the operation, the operator presses the fourth brake switch 108. The ninth and tenth electromagnetic brakes 52i, 52j are switched to the braking-off state from the braking-on state. The operator rotates the monitor 16 centering on the sixteenth rotation axis X16. The angle information of the monitor 16 with respect to the rotary arm 86 is detected by the tenth encoder 72j. A detection signal detected by the tenth encoder 72j is input into the second input section 114. The second input section 114 outputs the input detection signal to the second relative position calculation circuit 128. Based on the input detection signal, the second relative position calculation circuit 128 calculates the relative position of the display surface 16a of the monitor 16 with respect to the observation direction axis O1 of the endoscope 12 using the index 32c of the base 32a of the first holding device 14 and the index 82c of the base 82a of the second holding device 70 as the reference directions. The second relative position calculation circuit 128 outputs the relative position information to the second rotation number calculation circuit 130.

The second rotation number calculation circuit 130 calculates the necessary rotation numbers of the first and second motors 78a, 78b required for the display surface 16a of the monitor 16 to obtain the vertical state with respect to the endoscope 12 based on the input relative position information. The second rotation number calculation circuit 130 outputs the necessary rotation number information to the second driving circuit 132. The second driving circuit 132 produces the driving signal based on the input necessary rotation number information to drive and control the first and second motors 78a, 78b.

The first and second motors 78a, 78b rotate the first and second arms 36a, 36b centering on the fourth and fifth rotation axes X4 and X5. The first and second motors 78a, 78b rotate until the observation direction axis O1 of the endoscope 12 obtains the vertical state with respect to the display surface 16a of the monitor 16.

In a state in which the electromagnetic brakes 52i, 52j are switched to the braking-off state from the braking-on state, the monitor 16 is rotated centering on the fifteenth rotation axis X15. Angle information of the monitor 16 with respect to the second elevator arm 92 is detected by the ninth encoder 72i. The detection signal detected by the ninth encoder 72i is input into the second input section 114. The second input section 114 outputs the input detection signal to the second relative position calculation circuit 128. Based on the input detection signal, the second relative position calculation circuit 128 calculates the relative position of the display surface 16a of the monitor 16 with respect to the observation direction axis O1 of the endoscope 12 using the index 32c of the base 32a of the first holding device 14 and the index 82c of the base 82a of the second holding device 70 as the reference directions. The second relative position calculation circuit 128 outputs the relative position information to the second rotation number calculation circuit 130.

The second rotation number calculation circuit 130 calculates the necessary rotation numbers of the first and second motors 78a, 78b required for the display surface 16a of the monitor 16 to obtain the vertical state with respect to the endoscope 12 based on the input relative position information. The second rotation number calculation circuit 130 outputs the necessary rotation number information to the second driving circuit 132. The second driving circuit 132 produces the driving signal based on the input necessary rotation number information. The second driving circuit 132 drives and controls the first and second motors 78a, 78b. The first and second motors 78a, 78b rotate the first and second arms 36a, 36b centering on the fourth and fifth rotation axes X4 and X5. The first and second motors 78a, 78b rotate until the observation direction axis O1 of the endoscope 12 obtains the vertical state with respect to the display surface 16a of the monitor 16. In this manner, the first and second motors 78a, 78b set the observation direction axis O1 of the endoscope 12 into the mutual vertical state with respect to the display surface 16a of the monitor 16.

As described above, according to the present embodiment, the following can be said.

In the observation system 10, the endoscope 12 is movably disposed in the first holding device 14, and the monitor 16 is movably disposed in the second holding device 70, that is, the endoscope 12 and monitor 16 are separately disposed in the different holding devices 14, 70. Therefore, degree of freedom of the setting position of the monitor 16 can be enhanced, and usability of the observation system 10 can be enhanced.

The present embodiment is constituted in such a manner that the indexes 32c, 82c of the bases 32a, 82a are disposed to perform calibration, but the present invention is not limited to this constitution. For example, the calibration may also be performed using a known navigation system or the like.

Next, a fourth embodiment will be described with reference to FIGS. 8 and 9. This embodiment is a modification of the third embodiment, the same members as those described in the third embodiment are denoted with the same reference numerals, and the detailed description is omitted.

Figure 8:
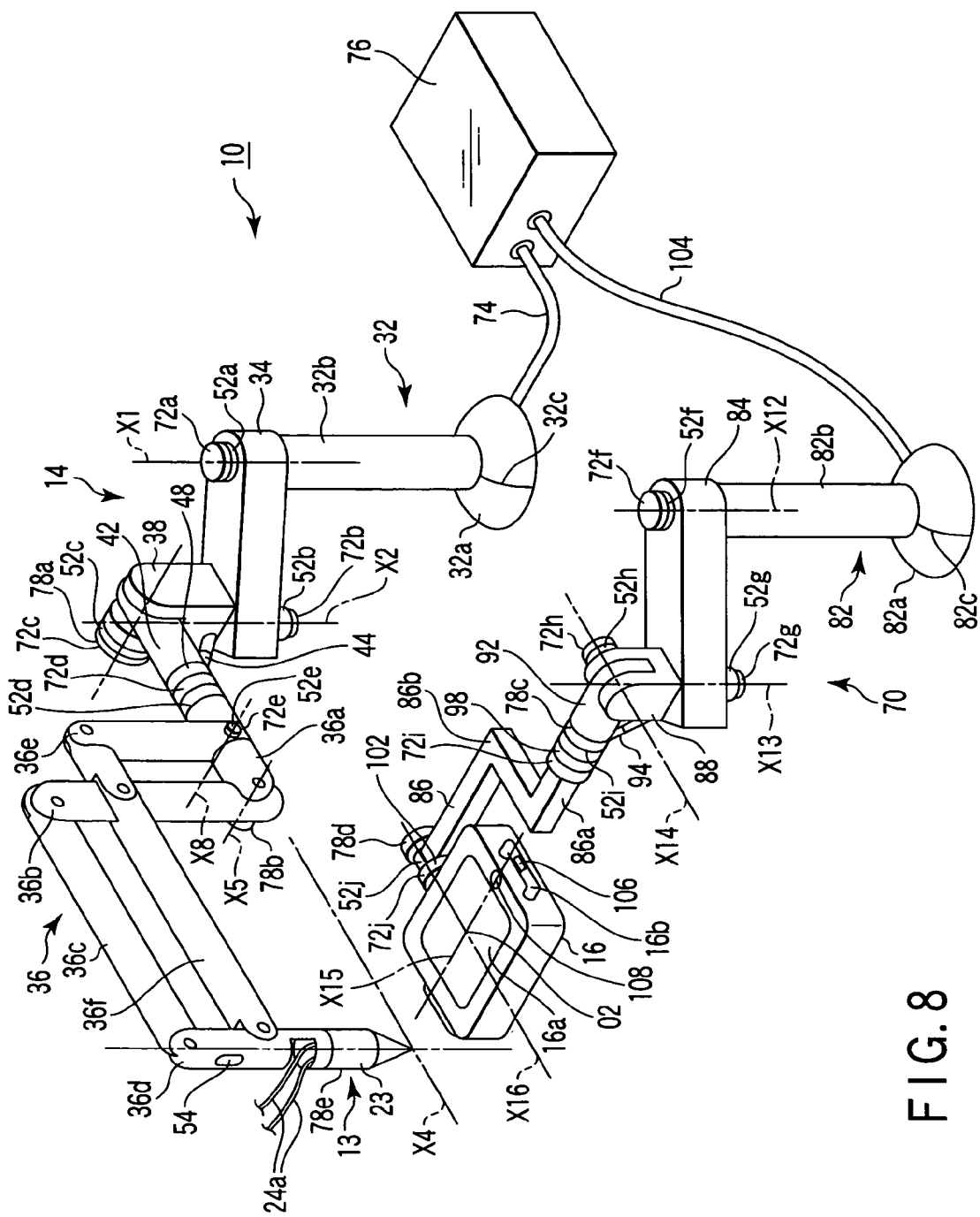
FIG. 8 is a perspective view showing a schematic configuration of the observation system according to a fourth embodiment of the present invention.

As shown in FIG. 8, in the observation system 10 according to the present embodiment, instead of the endoscope 12, a fifth motor 78e, and the microscope body 23 of the electronic image microscope 13 (see FIG. 5 for the inner constitution) are disposed. The fifth motor 78e is attached to the lower end portion of the fourth arm 36d. The microscope body 23 of the electronic image microscope 13 is attached to the fifth motor 78e. The rotation axes of the fifth motor 78e and microscope body 23 match a longitudinal axis O1 of the fourth arm 36d. Therefore, the microscope body 23 of the electronic image microscope 13 rotates with respect to the fourth arm 36d, when the fifth motor 78e is rotated.

Figure 9:
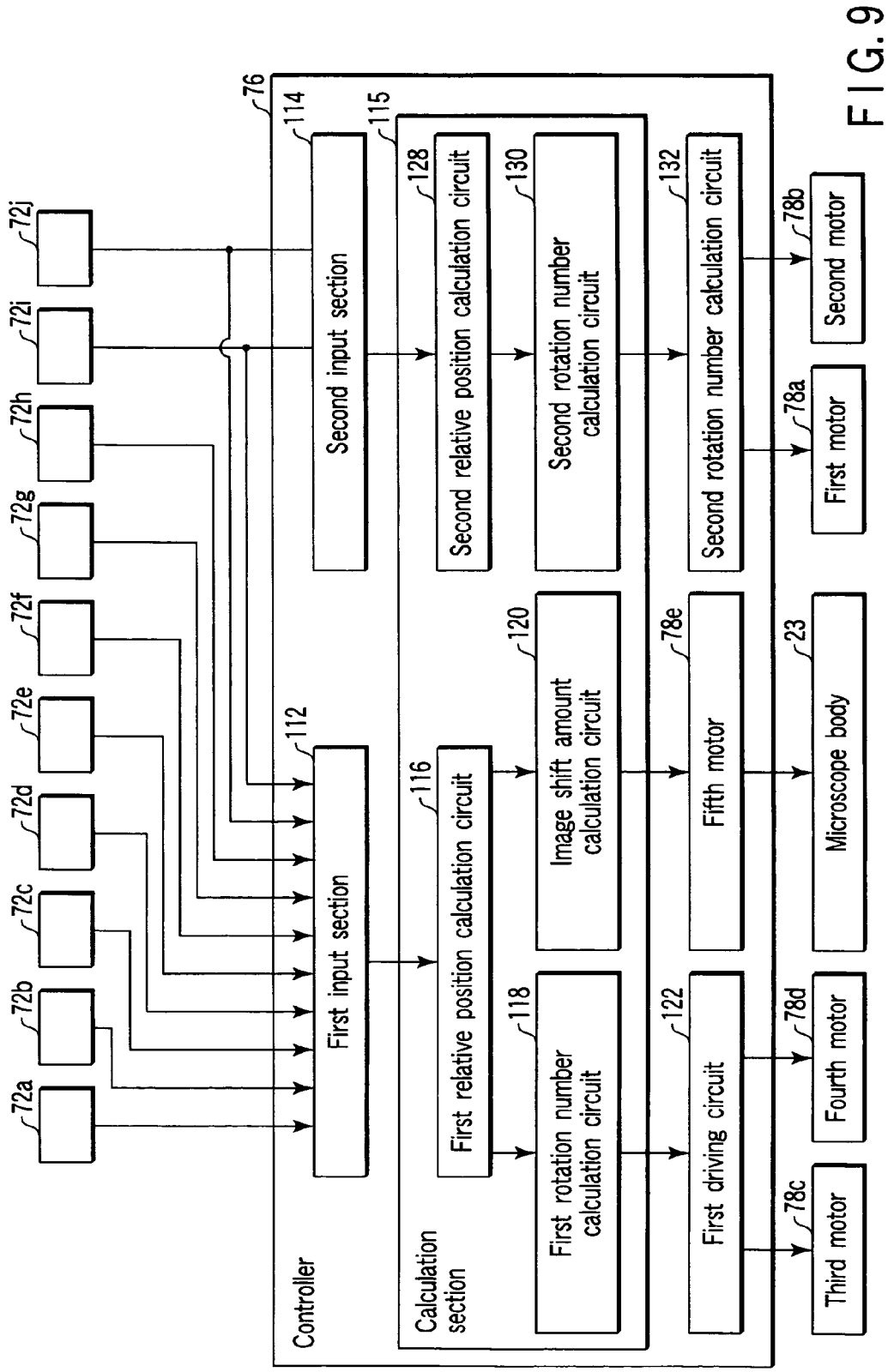
FIG. 9 is a block diagram showing the control system of the observation system according to the fourth embodiment.

As shown in FIG. 9, the output end of the image shift amount calculation circuit 120 of the controller 76 is connected to the signal input end of the fifth motor 78e. As described above, the fifth motor 78e is connected to the microscope body 23 of the electronic image microscope 13.

Next, a function of the observation system 10 according to the present embodiment will be described.

The operator presses the third brake switch 106 in a state in which the grip 16b of the monitor 16 is grasped, and disposes the monitor 16 in an optional position.

As described in the third embodiment, the operator presses the first brake switch 54 to three-dimensionally move the microscope body 23 so that the patient's operative part 200 can be observed. At this time, the first to fifth encoders 72a to 72e of the first holding device 14 output the detected signals to the controller 76 via the cable 74. Similarly, the sixth to tenth encoders 72f to 72j output the detected signals to the controller 76 via the cable 74. That is, the angle information detected by the first to tenth encoders 72a to 72j is input into the first input section 112 shown in FIG. 9. The first input section 112 outputs the input angle information to the first relative position calculation circuit 116.

The first relative position calculation circuit 116 calculates the relative position of the display surface 16a of the monitor 16 with respect to the observation direction axis O1 of the microscope body 23 using the index 32c of the first base 32a and the index 82c of the second base 82a as the reference directions based on the input angle information. The first relative position calculation circuit 116 outputs the relative position information to the first rotation number calculation circuit 118.

The first rotation number calculation circuit 118 calculates the necessary rotation numbers of the third and fourth motors 78c, 78d required for the display surface 16a of the monitor 16 to obtain the vertical state with respect to the observation direction axis O1 of the microscope body 23 based on the input relative position information. The first rotation number calculation circuit 118 outputs the necessary rotation number information to the image shift amount calculation circuit 120 and first driving circuit 122.

The first driving circuit 122 produces the driving signal based on the input necessary rotation number information to drive and control the third and fourth motors 78c, 78d. The third and fourth motors 78c, 78d rotate the rotary arm 86 and monitor 16 centering on the fifteenth and sixteenth rotation axes X15 and X16. The third and fourth motors 78c, 78d rotate until the observation direction axis O1 of the microscope body 23 obtains the vertical state with respect to the display surface 16a of the monitor 16.

The image shift amount calculation circuit 120 calculates the shifts of the vertical/horizontal directions of the image picked up by the image pickup devices 23dR, 23dL of the microscope body 23 and the display surface 16a of the monitor 16 to calculate the image shift amount based on the relative position information input from the first relative position calculation circuit 116. The image shift amount calculation circuit 120 outputs a rotation amount of the microscope body 23 around the axis O1, required for correcting the calculated image shift amount, to the fifth motor 78e. The microscope body 23 is rotated around the axis O1 by the fifth motor 78e to match the moving direction of the view field by the moving of the microscope body 23 with that on the monitor 16. That is, the image displayed on the display surface 16a of the monitor 16 is rotated, and the positional relation of two right/left image pickup devices 23dR, 23dL in the microscope body 23 with respect to the operator is controlled to match a positional relation of the operator's eyes with respect to the monitor 16.

Next, to move the operation field, the operator moves the monitor 16 around the fifteenth and sixteenth rotation axes X15 and X16. The positional relation is calculated by the outputs of the first to tenth encoders 72a to 72j, and the fifth motor 78e of the fourth arm 36d which supports the microscope body 23 is driven. At this time, the position of the microscope body 23 is controlled to keep the optical axis O1 of the microscope body 23 in the vertical state with respect to the display surface 16a of the monitor 16. In this case, the optical axis O1 of the microscope body 23 is constantly kept in the vertical state with the display surface 16a of the monitor 16. Therefore, while the operator sees the display surface 16a of the monitor 16, the operator can easily grasp the angle and direction of the operative part obtained using the electronic image microscope 13.

Next, a fifth embodiment will be described with reference to FIGS. 10 to 16B. The embodiment is a modification of the third embodiment, the same members as those described in the third embodiment are denoted with the same reference numerals, and the detailed description is omitted.

Figure 10:
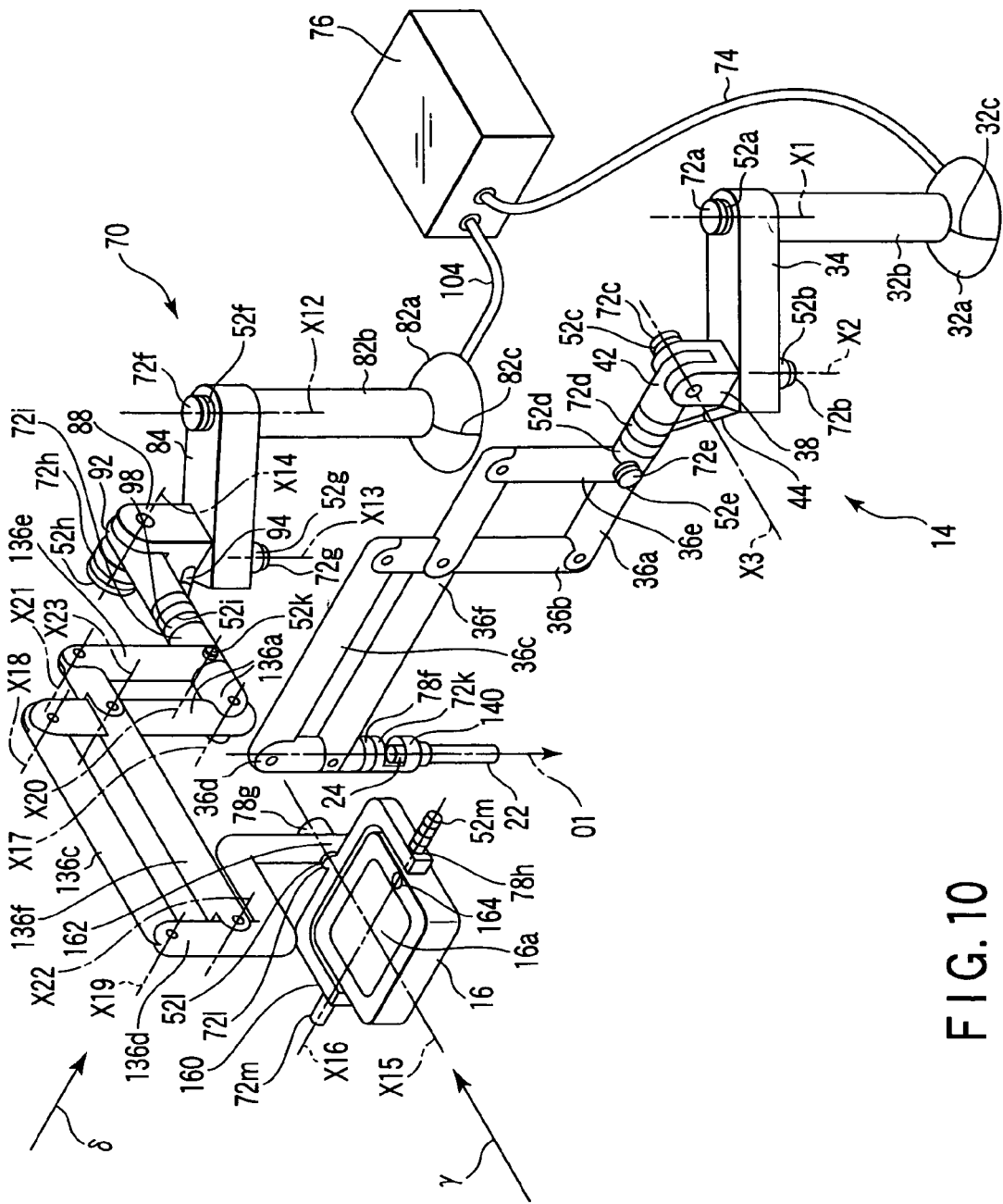
FIG. 10 is a perspective view showing a schematic configuration of the observation system according to a fifth embodiment of the present invention.

As shown in FIG. 10, in the present embodiment, unlike the third embodiment, the second holding device 70 by which the monitor 16 is held includes a second parallel link mechanism 136 instead of the rotary arm 86. A bendable curved mechanism is disposed in the insertion section 22 of the endoscope 12 held by the first holding device 14.

An endoscope holding portion 140 is disposed in the distal portion of the fourth arm 36d of the first parallel link mechanism 36 of the first holding device 14 in which the endoscope 12 is held. The endoscope holding portion 140 includes a sixth motor (image rotation mechanism) 78f and an eleventh encoder 72k. The endoscope 12 is detachably attached to the lower end portion of the endoscope holding portion 140 to be rotatable by the sixth motor 78f. The eleventh encoder 72k detects the angle around the observation direction axis O1 with respect to the fourth arm 36d. The direction of the image obtained by the endoscope 12 when rotating and controlling the sixth motor 78f is appropriately selected based on detected angle information.

The second parallel link mechanism 136 is disposed on the fourth bearing portion 98 of the other end portion of the elevator arm 92 in the second holding device 70. The parallel link mechanism 136 includes first to sixth arms 136a to 136f.

One end portion of the first arm 136a is supported by the fourth bearing portion 98. The axial direction of the first arm 136a matches the fifteenth rotation axis X15. Therefore, the first arm 136a is rotatable around the fifteenth rotation axis X15 by the fourth bearing portion 98.

The lower end portion of the second arm 136b is supported rotatably around a seventeenth rotation axis X17 in the other end portion of the first arm 136a. The upper end portion of the second arm 136b is supported rotatably around an eighteenth rotation axis X18 in one end portion of the third arm 136c. The other end portion of the third arm 136c is supported rotatably around a nineteenth rotation axis X19 in the upper end portion of the fourth arm 136d.

The lower end portion of the fifth arm 136e is supported rotatably around a twentieth rotation axis X20 between one end portion and the other end portion of the first arm 136a. The fifth arm 136e is parallel to the second arm 136b. The upper end portion of the fifth arm 136e is supported rotatably around a twenty-first rotation axis X21 in one end portion of the sixth arm 136f. The sixth arm 136f is parallel to the third arm 136c. The other end portion of the sixth arm 136f is supported rotatably around a twenty-second rotation axis X22 in the fourth arm 136d. The sixth arm 136f and second arm 136b are supported rotatably around a twenty-third rotation axis X23. The second parallel link mechanism 136 is formed in this manner.

An eleventh electromagnetic brake 52k is disposed on the connecting portion of the first arm 136a with the fifth arm 136e. The eleventh electromagnetic brake 52k is switchable to a braking-on state in which the rotation of the fifth arm 136e around the twentieth rotation axis X20 is electrically controlled and a braking-off state in which the rotation around the twentieth rotation axis X20 is allowed.

A substantially U-shaped monitor holding portion 160 which holds the monitor 16 is disposed in the lower end portion of the fourth arm (second holding portion) 136d. The monitor holding portion 160 is disposed rotatably around the fifteenth rotation axis X15 by a support portion 162 of the lower end portion of the fourth arm 136d. A seventh motor 78g, twelfth electromagnetic brake 52l, and twelfth encoder 72l are disposed in the support portion 162. These seventh motor 78g, twelfth electromagnetic brake 52l, and twelfth encoder 72l are connected to the controller 76 via the cable 104.

The monitor 16 is attached to the monitor holding portion 160 rotatably centering on the sixteenth rotation axis X16. An eighth motor 78h, thirteenth electromagnetic brake 52m, and thirteenth encoder 72m are disposed on the connecting portion of the monitor 16 with the monitor holding portion 160. These eighth motor 78h, thirteenth electromagnetic brake 52m, and thirteenth encoder 72m are connected to the controller 76 via the cable 104. In this case, the thirteenth encoder 72m detects the rotation angle of the monitor holding portion 160 around the sixteenth rotation axis X16 to output the angle to the controller 76. The eighth motor 78h rotates the monitor 16 around the sixteenth rotation axis X16 in response to the driving signal from the controller 76.

A fifth brake switch 164 is disposed in the monitor 16. The switch 164 can switch the ninth, eleventh to thirteenth electromagnetic brakes 52i, 52k to 52m to the braking-off state from the braking-on state in response to the operation.

Next, a constitution of a bending mechanism for bending a bendable portion 22b of the endoscope 12 will be described with reference to FIGS. 11A and 11B.

Figure 11A:
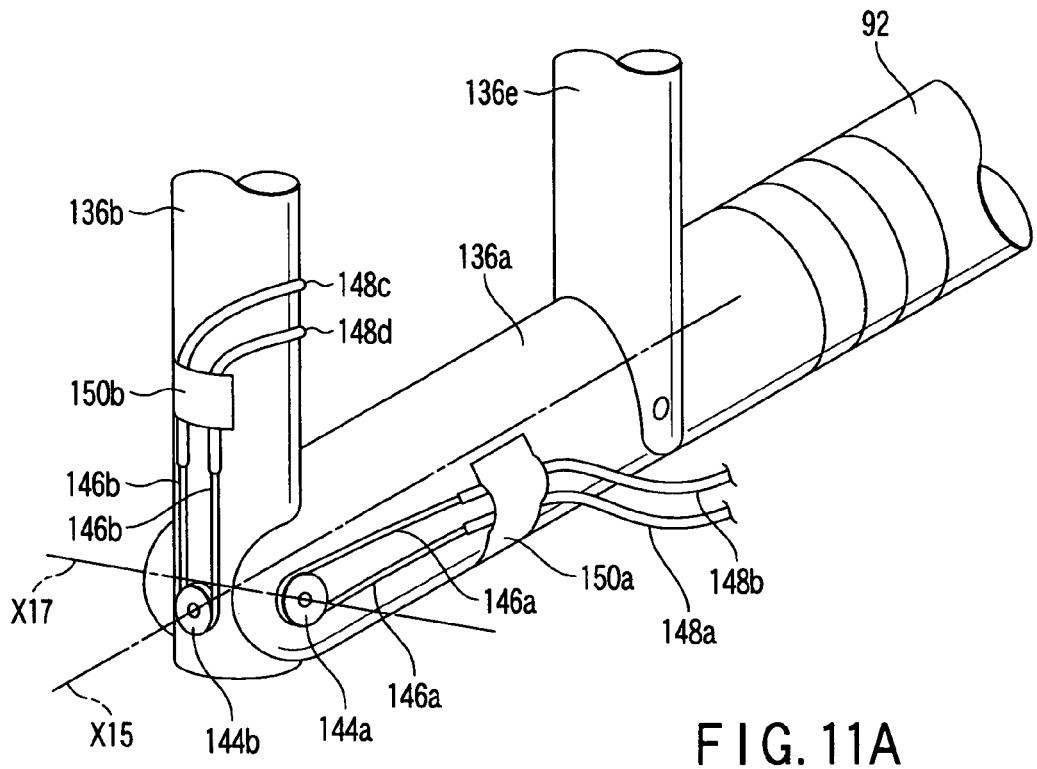
FIG. 11A is perspective view showing a structure in the vicinity of first and second arms of a second parallel link mechanism of a second holding device in the observation system according to a fifth embodiment.
Figure 11B:
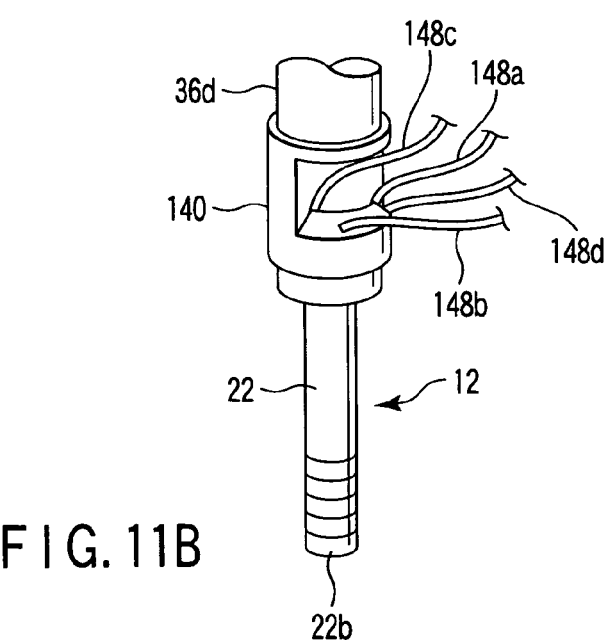
FIG. 11B is a schematic perspective view showing the insertion section of the endoscope in the observation system according to the fifth embodiment.

As shown in FIG. 11A, a first pulley 144a is attached rotatably centering on the fifteenth rotation axis X15 on the fifteenth rotation axis X15 of the other end portion of the first arm 136a of the second parallel link mechanism 136 in the second holding device 70. A first wire 146a is hooked on the first pulley 144a. The wire 146a is passed through first and second tubes 148a, 148b fixed to the first arm 136a by a first fixing plate 150a. As shown in FIG. 11B, one end portion of each of the tubes 148a, 148b is attached to the endoscope 12 disposed in the first holding device 14.

As shown in FIG. 11A, a second pulley 144b is attached rotatably centering on the seventeenth rotation axis X17 on the seventeenth rotation axis X17 of the lower end portion of the second arm 136b of the second parallel link mechanism 136 in the second holding device 70. A second wire 146b is hooked on the pulley 144b. The wire 146b is passed through third and fourth tubes 148c, 148d fixed to the second arm 136b by a second fixing plate 150b. As shown in FIG. 11B, one end portion of each of the tubes 148c, 148d is attached to the endoscope 12 disposed in the first holding device 14.

Although not shown, the bendable portion 22b of the endoscope 12 is connected to the first and second wires 146a, 146b. The end portions of these wires 146a, 146b are disposed in positions deviating from the center of the bendable portion 22b every 90°, and a pair of end portions of the wires 146a, 146b are disposed in positions facing each other. Therefore, when the first and second wires 146a, 146b are moved forwards/backwards, it is possible to bend the bendable portion 22b in the desired direction.

Figure 12:
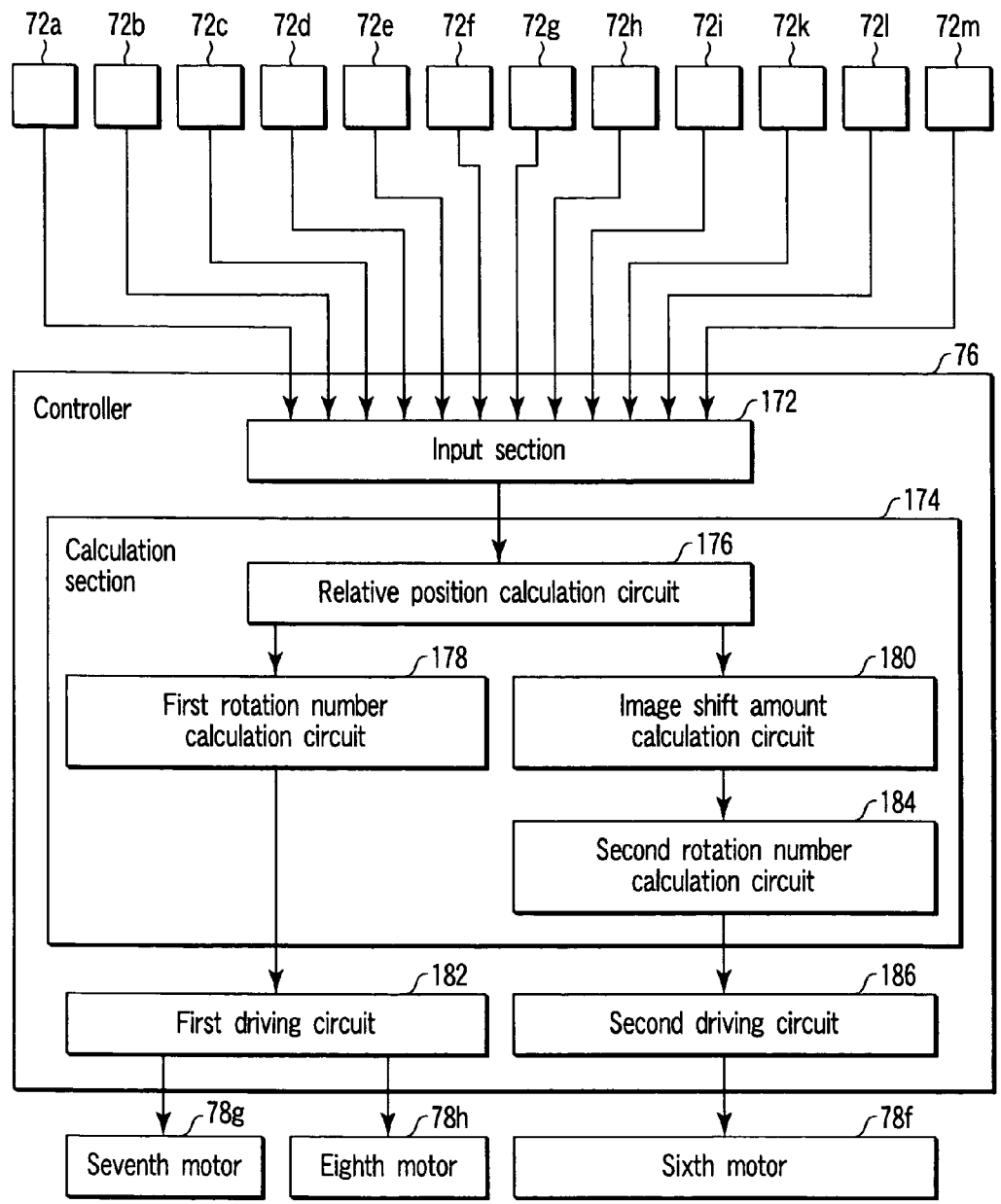
FIG. 12 is a block diagram showing the control system of the observation system according to the fifth embodiment.

As shown in FIG. 12, an input section 172 is disposed in the controller 76. The input section 172 is connected to the output ends of the first to fifth, seventh to ninth, eleventh to thirteenth encoders 72a to 72e, 72g to 72i, 72k to 72m. The output end of the input section 172 is connected to a relative position calculation circuit 176 of a calculation section 174 constituting the calculation means. The output end of the relative position calculation circuit 176 is connected to a first rotation number calculation circuit 178 and an image shift amount calculation circuit 180. The output end of the first rotation number calculation circuit 178 is connected to a first driving circuit 182. The first driving circuit 182 is connected to the signal input ends of the seventh and eighth motors 78g, 78h. The output end of the image shift amount calculation circuit 180 is connected to a second rotation number calculation circuit 184. The output end of the second rotation number calculation circuit 184 is connected to a second driving circuit 186. The second driving circuit 186 is connected to the signal input end of the sixth motor 78f.

Next, the function of the observation system 10 according to the present embodiment will be described. Here, a function of disposing the monitor 16 in a position which is easy for the operator to see, and a function of disposing the distal portion of the insertion section 22 of the endoscope 12 in the desired position in the patient's operative part 200 and in the desired direction will be described.

As described in the first embodiment, the operator presses the first brake switch 54 to three-dimensionally move the endoscope 12, and the distal portion of the insertion section 22 of the endoscope 12 is disposed in the desired position in the patient's operative part 200 and in the desired direction.

The first encoder 72a of the first holding device 14 detects the angle of the first revolving arm 34 with respect to the first support mechanism 32. The second encoder 72b detects the angle of the first revolving arm 34 with respect to the first bearing portion 38. The third encoder 72c detects the angle of the first elevator arm 42 with respect to the first bearing portion 38. The fourth encoder 72d detects the angle of the first arm 36a with respect to the first elevator arm 42. The fifth encoder 72e detects the angle of the fifth arm 36e with respect to the first arm 36a. These first to fifth encoders 72a to 72e output the detected signals to the controller 76 via the cable 74.

The function of disposing the monitor 16 in the position which is easy for the operator to see will be described.

The operator presses the fifth brake switch 164 in the grasped state of the grip 16b of the monitor 16.

The sixth to ninth, eleventh to thirteenth electromagnetic brakes 52f to 52i, 52k to 52m are switched to the braking-off state from the braking-on state all together. In this state, the operator rotates and deforms the second holding device 70 of the observation system 10 around the twelfth to twenty-third rotation axes X12 to X23.

When the controls of the sixth and seventh electromagnetic brakes 52f, 52g are released, the operator can adjust the horizontal direction position of the monitor 16. When the control of the eighth electromagnetic brake 52h is released, the operator can adjust the vertical direction position of the monitor 16.

When the control of the ninth electromagnetic brake 52i is released, the rotary arm 86 is entirely rotatable centering on the fifteenth rotation axis X15 by the rotary arm 86. Therefore, the operator can incline the monitor 16 in the desired direction.

When the control of the tenth electromagnetic brake 52j is released, the monitor 16 is rotatable centering on the sixteenth rotation axis X16. Therefore, the operator can adjust the horizontal state of the display surface 16a of the monitor 16.

By the combination of the movement of the second holding device 70, the operator sets the display surface 16*a* of the monitor 16 in the position which is easy for the operator to see.

Moreover, the sixth to ninth encoders 72*f* to 72*i* of the second holding device 70 output the detected signals to the controller 76 via the cable 104. The eleventh encoder 72*k* detects the rotation angle of the insertion section 22 of the endoscope 12 with respect to the fourth arm 36*d* of the first holding device 14. The twelfth encoder 72*l* detects the angle of the monitor holding portion 160 with respect to the fourth arm 136*d* of the second holding device 70. The thirteenth encoder 72*m* detects the angle of the monitor 16 with respect to the monitor holding portion 160. The eleventh to thirteenth encoders 72*k* to 72*m* output the detected signals to the controller 76 via the cables 74, 104.

The detected signals from the first to ninth, eleventh to thirteenth encoders 72*a* to 72*i*, 72*k* to 72*m* are input into the input section 172. The input section 172 outputs the respective detected signals to the relative position calculation circuit 176. The relative position calculation circuit 176 calculates the relative position of the display surface 16*a* of the monitor 16 with respect to the observation direction axis O1 of the endoscope 12 using the indexes 32*c*, 82*c* of the bases 32*a*, 82*a* which are reference directions based on the input detected signals. The relative position calculation circuit 176 outputs the relative position information to the first rotation number calculation circuit 178.

The first rotation number calculation circuit 178 calculates the necessary rotation numbers of the seventh and eighth motors 78*g*, 78*h* required for the display surface 16*a* of the monitor 16 to obtain the vertical state with respect to the observation direction axis O1 of the endoscope 12 based on the input relative position information. The first rotation number calculation circuit 178 outputs the necessary rotation number information to the first driving circuit 182.

The first driving circuit 182 produces a driving signal based on the input necessary rotation number information to drive and control the seventh and eighth motors 78*g*, 78*h*. The seventh and eighth motors 78*g*, 78*h* selectively rotate and control the monitor holding portion 160 and monitor 16 centering on the fifteenth and sixteenth rotation axes X15 and X16. The seventh and eighth motors 78*g*, 78*h* rotate until the display surface 16*a* of the monitor 16 obtains the vertical state with respect to the observation direction axis O1 of the endoscope 12.

Moreover, the relative position calculation circuit 176 outputs the relative position information to the image shift amount calculation circuit 180. The image shift amount calculation circuit 180 calculates the shifts of the vertical/horizontal directions of the image picked up by the TV camera 24 and the display surface 16*a* of the monitor 16 to calculate the image shift amount based on the relative position information. Based on the input image shift amount, the second rotation number calculation circuit 184 calculates the necessary rotation number of the sixth motor 78*f* for rotating the holding portion 140 with respect to the fourth arm 36*d* centering on the observation direction axis O1 of the insertion section 22 of the endoscope 12. The rotation number is required to match the moving direction of the view field by the moving of the endoscope 12 with that on the monitor 16. The second rotation number calculation circuit 184 outputs the necessary rotation number information to the second driving circuit 186.

The second driving circuit 186 produces a driving signal based on the input necessary rotation number information. The second driving circuit 186 outputs the driving signal to the sixth motor 78*f*. The sixth motor 78*f* rotates and controls the holding portion 140 centering on the observation direction axis O1 with respect to the fourth arm 36*d*. The sixth motor 78*f* sets the same moving direction of the view field of the endoscope 12 as that on the monitor 16.

Next, to change the view field direction of the endoscope 12 during the operation, the operator presses the fifth brake switch 164. The ninth, eleventh to thirteenth electromagnetic brakes 52*i*, 52*k* to 52*m* are switched to the braking-off state from the braking-on state.

As shown in FIG. 13A, the monitor 16 disposed in the second parallel link mechanism 136 of the second holding device 70 is rotated, for example, in an arrow IIIa direction centering on the fifteenth rotation axis X15. The whole second parallel link mechanism 136 rotates in the arrow IIIa direction centering on the fifteenth rotation axis X15. That is, the first arm 136*a* rotates in the arrow IIIa direction centering on the fifteenth rotation axis X15 with respect to the second pulley 144*b* of the second arm 136*b*.

The second wire 146*b* moves forwards/backwards by the second pulley 144*b*. Concretely, as shown in FIG. 13B, on an endoscope 12 side of the first parallel link mechanism 36 of the first holding device 14, the second wire 146*b* disposed in a third tube 148*c* moves in an arrow IVa direction in FIG. 13B. The second wire 146*b* disposed in a fourth tube 148*d* moves in an arrow IVb direction opposite to the arrow IVa direction in FIG. 13B. Therefore, the bendable portion 22*b* of the endoscope 12 bends while keeping the observation direction in the vertical state with respect to the display surface 16*a* of the monitor 16.

As shown in FIG. 14A, the monitor 16 is rotated, for example, in an arrow IIIb direction centering on the fifteenth rotation axis X15. The whole second parallel link mechanism 136 rotates in the arrow IIIb direction centering on the fifteenth rotation axis X15. That is, the first arm 136*a* rotates in the arrow IIIb direction centering on the fifteenth rotation axis X15 with respect to the second pulley 144*b* of the second arm 136*b*.

The second wire 146*b* moves forwards/backwards by the second pulley 144*b*. Concretely, as shown in FIG. 14B, on the endoscope 12 side, the second wire 146*b* disposed in the third tube 148*c* moves in an arrow IVb direction in FIG. 14B. The second wire 146*b* disposed in the fourth tube 148*d* moves in a direction opposite to an arrow IVd direction in FIG. 14B. Therefore, the bendable portion 22*b* of the endoscope 12 bends while keeping the observation direction in the vertical state with respect to the display surface 16*a* of the monitor 16.

Figure 15A:
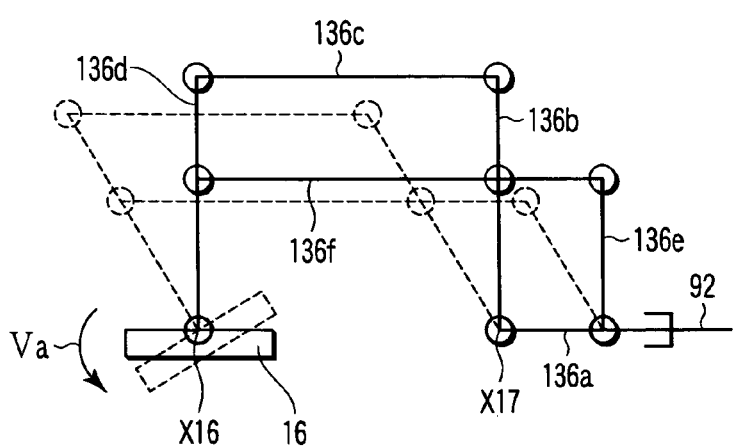
FIG. 15A is a schematic diagram showing that the operation of the parallel link mechanism of the observation system is observed from an arrow δ direction in FIG. 10 in the observation system according to the fifth embodiment, a solid line shows the parallel state of the monitor with respect to the floor surface, and a broken line shows a state in which the monitor is rotated in an arrow Va direction.

As shown in FIG. 15A, the monitor 16 disposed in the second parallel link mechanism 136 of the second holding device 70 is rotated, for example, in an arrow Va direction centering on the sixteenth rotation axis X16. The whole second parallel link mechanism 136 rotates in the arrow Va direction by an angle equal to that of the sixteenth rotation axis X16 in synchronization with the rotation of the monitor 16. That is, the second arm 136*b* rotates in the arrow Va direction centering on the seventeenth rotation axis X17 with respect to the first pulley 144*a* of the first arm 136*a*.

Figure 15B:
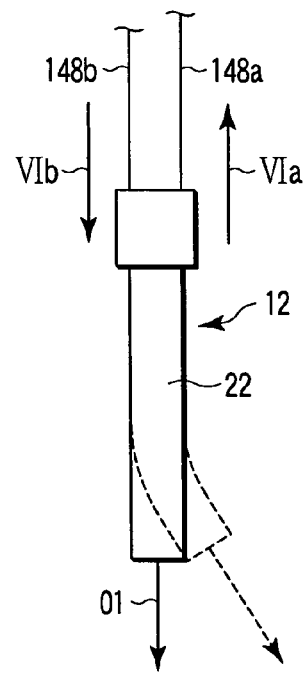
FIG. 15B is a schematic diagram of the insertion section of the endoscope in the observation system according to the fifth embodiment, a solid line shows a state in which the insertion section of the endoscope crosses the floor surface at right angles, and a broken line shows a curved state of the curved portion of the insertion section of the endoscope, curved in conjunction at a time when the monitor is rotated in the arrow Va direction in FIG. 15A.

The first wire 146*a* moves forwards/backwards by the first pulley 144*a*. Concretely, as shown in FIG. 15B, on the endoscope 12 side of the first parallel link mechanism 36 of the first holding device 14, the first wire 146*a* disposed in a first tube 148*a* moves in an arrow VIa direction in FIG. 15B. The first wire 146*a* disposed in a second tube 148*b* moves in an arrow VIb direction opposite to the arrow VIa direction in FIG. 15B. Therefore, the bendable portion 22*b* of the endoscope 12 bends while keeping the observation direction in the vertical state with respect to the display surface 16a of the monitor 16.

Figure 16A:
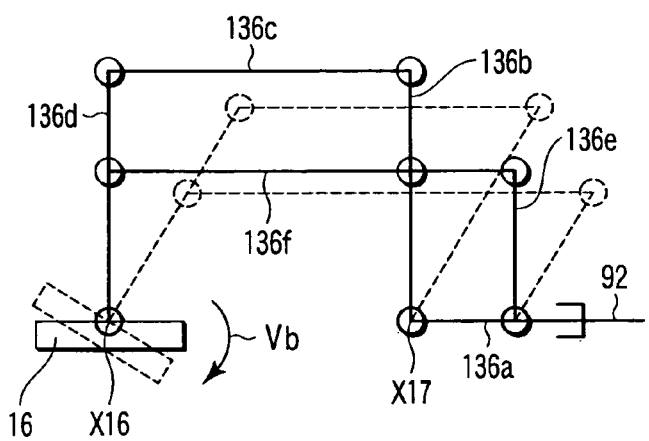
FIG. 16A is a schematic diagram showing that the operation of the parallel link mechanism of the observation system is observed from the arrow δ direction in FIG. 10 in the observation system according to the fifth embodiment, a solid line shows the parallel state of the monitor with respect to the floor surface, and a broken line shows a state in which the monitor is rotated in an arrow Vb direction.

As shown in FIG. 16A, the monitor 16 is rotated, for example, in an arrow Vb direction centering on the sixteenth rotation axis X16. The whole second parallel link mechanism 136 rotates in the arrow Vb direction by the angle equal to that of the sixteenth rotation axis X16 in synchronization with the rotation of the monitor 16. That is, the second arm 136b rotates in the arrow Vb direction centering on the seventeenth rotation axis X17 with respect to the first pulley 144a of the first arm 136a.

Figure 16B:
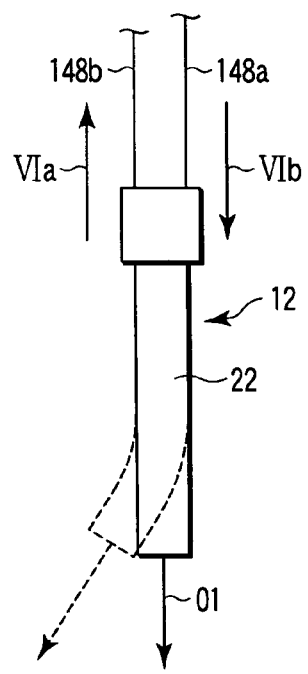
FIG. 16B is a schematic diagram of the insertion section of the endoscope in the observation system according to the fifth embodiment, a solid line shows a state in which the insertion section of the endoscope crosses the floor surface at right angles, and a broken line shows a curved state of the curved portion of the insertion section of the endoscope, curved in conjunction at a time when the monitor is rotated in the arrow Vb direction in FIG. 16A.

The first wire 146a moves forwards/backwards by the first pulley 144a. Concretely, as shown in FIG. 16B, on the endoscope 12 side, the first wire 146a disposed in the first tube 148a moves in an arrow VIb direction in FIG. 16B. The first wire 146a disposed in the second tube 148b moves in an arrow VIa direction opposite to the arrow VIb direction in FIG. 16B. Therefore, the bendable portion 22b of the endoscope 12 bends while keeping the observation direction in the vertical state with respect to the display surface 16a of the monitor 16.

As described above, according to the present embodiment, the following can be said.

In addition to mechanism for rotating the endoscope 12 to change the observation direction as described in the third embodiment, by the constitution combined with the endoscope 12 including the bending mechanism, the view field of the endoscope 12 can be moved with a small movement. Therefore, the observation direction can be changed in a broad range even in a deep and narrow operative part.

In the embodiment, a case has been described in which the indexes 32c, 82c are disposed in the respective bases 32a, 82a to perform mutual calibration on the sides of the endoscope 12 and monitor 16, but the present invention is not limited to this constitution. For example, the calibration may also be performed using a known navigation system or the like in the same manner as in the third embodiment.

In the first to fifth embodiments, a constitution has been described in which the parallel link mechanism is disposed in the first holding device 14 to constitute the equivalent movement mechanism, but the present invention is not limited to this constitution. The equivalent movement mechanism may also be constituted, for example, using a timing belt instead of the parallel link mechanism. That is, a first mechanism which holds the endoscope may also be connected to a second mechanism which holds the display device via the timing belt.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. An observation system comprising:
   an observation device including an optical objective system for observation of an object;
   an image pickup device which picks up an optical image incident upon the optical objective system of the observation device;
   a display device which is electrically connected to the image pickup device and which displays the optical image picked up by the image pickup device; and
   at least one holding mechanism including:
   a moving mechanism which includes a first moving mechanism which movably holds the observation device and a second moving mechanism which movably holds the display device, the moving mechanism being effective to move one of the observation device and the display device in conjunction with movement of the other device; and
   a switching mechanism capable of switching the observation device and the display device to a state in which the devices are movable by the moving mechanism and a state in which the devices are fixable in positions moved by the moving mechanism.

2. An observation system according to claim 1, wherein the moving mechanism comprises:
   a vertical movement mechanism capable of moving the observation device and the display device in a vertical direction;
   a horizontal movement mechanism capable of moving the observation device and the display device in a horizontal direction;
   an inclination mechanism which inclines the observation device and the display device; and
   an equivalent movement mechanism in which the observation device and the display device are disposed and which mutually equivalently moves the observation device and the display device.

3. An observation system according to claim 2, wherein the equivalent movement mechanism comprises a timing belt which connects a first mechanism which holds the observation device to a second mechanism which holds the display device.

4. An observation system according to claim 1, wherein the holding mechanism comprises:
   a first holding device which holds the observation device; and
   a second holding device which holds the display device.

5. An observation system according to claim 4, wherein a control device to control a display surface of the display device and an optical axis of the observation device in a state in which the display surface and the optical axis cross each other at right angles is connected to the first and second holding devices.

6. An observation system according to claim 5, wherein the control device comprises:
   a first detection section which detects posture of the observation device;
   a second detection section which detects posture of the display device;
   a calculation section which calculates relative positions of the observation device and the display device from detected amounts detected by the first and second detection sections; and
   a posture adjustment section which adjusts the posture of at least one of the observation device and the display device in accordance with a calculation result of the calculation section.

7. An observation system according to claim 6, wherein the posture adjustment section comprises a motor being controlled by rotation number in accordance with the calculation result of the calculation section.

8. An observation system according to claim 6, wherein the first detection section comprises a plurality of encoders disposed in the first holding device, and
   the second detection section comprises a plurality of encoders disposed in the second holding device.

9. An observation system according to claim 5, wherein the control device comprises:
a first detection section which detects posture of the observation device;
a second detection section which detects posture of the display device;
a relative position calculation section which calculates relative positions of a view field direction of the image pickup device and a view field direction displayed in the display device from detected amounts detected by the first and second detection sections; and
an image rotation section which rotates an image displayed in the display device in accordance with a calculation result from the relative position calculation section.

10. An observation system according to claim 9, wherein the first detection section comprises a plurality of encoders disposed in the first holding device, and
the second detection section comprises a plurality of encoders disposed in the second holding device.

11. An observation system according to claim 5, wherein the first and second holding devices comprise indexes which calibrate the relative positions between the holding devices.

12. An observation system according to claim 1, wherein the observation device comprises an insertion section of an endoscope, and
the insertion section comprises a bendable portion.

13. An observation system according to claim 12, wherein a coupling mechanism is disposed between the insertion section and the display device, in which the bendable portion is bent with the movement of the display device and the display device is moved with the bending of the bendable portion.

14. An observation system according to claim 1, wherein the observation device comprises an electronic image microscope.

15. An observation system according to claim 14, wherein the electronic image microscope comprises a stereoscopic observation mechanism.

16. An observation system comprising:
an observation device including an optical objective system for observation of an object;
an image pickup device which picks up an optical image incident upon the optical objective system of the observation device;
a display device which is electrically connected to the image pickup device and which displays the optical image picked up by the image pickup device; and
at least one holding mechanism including a moving mechanism which holds the observation device and the display device and which moves one of the observation device and the display device in conjunction with movement of the other device, and a switching mechanism capable of switching the observation device and the display device to a state in which the devices are movable by the moving mechanism and a state in which the devices are fixable in positions moved by the moving mechanism, wherein the moving mechanism comprises:
a vertical movement mechanism capable of moving the observation device and the display device in a vertical direction;
a horizontal movement mechanism capable of moving the observation device and the display device in a horizontal direction;
an inclination mechanism which inclines the observation device and the display device; and
an equivalent movement mechanism in which the observation device and the display device are disposed and which mutually equivalently moves the observation device and the display device,
wherein the equivalent movement mechanism comprises a first parallelogram link in which the observation device is disposed, and a second parallelogram link in which the display device is disposed, and
the first and second parallelogram links comprise a parallel link mechanism connected to at least a common arm among arms constituting the first and second parallelogram links.

17. An observation system according to claim 16, wherein the parallel link mechanism comprises:
a first arm comprising one end portion and the other end portion, the one end portion being connected to the inclination mechanism;
a second arm comprising an upper end portion and a lower end portion, the lower end portion being connected to the other end portion of the first arm;
a third arm comprising one end portion and the other end portion, the one end portion being connected to the upper end portion of the second arm, the third arm being disposed in parallel with the first arm;
a fourth arm comprising an upper end portion, and a lower end portion which holds the endoscope, the upper end portion being connected to the other end portion of the third arm, the fourth arm being disposed in parallel with the second arm;
a fifth arm comprising an upper end portion and a lower end portion, the lower end portion being connected between the one end portion and the other end portion of the first arm, the fifth arm being disposed in parallel with the second arm; and
a sixth arm comprising one end portion and the other end portion, the one end portion being connected to the upper end portion of the fifth arm, the other end portion being connected to the fourth arm, the one end portion and the other end portion being connected between the upper and lower end portions of the second arm, the sixth arm being disposed in parallel with the first arm,
wherein the second, third, fourth, and sixth arms form the first parallelogram link, and
the first, second, fifth, and sixth arms form the second parallelogram link.

18. An observation system according to claim 17, wherein the display device is disposed on a connecting portion of the other end portion of the first arm with the lower end portion of the second arm, and
a central axis of the observation device is in a vertical state with respect to a display surface of the display device.

19. An observation system according to claim 18, wherein the observation device includes an insertion section of the endoscope, and
the optical objective system of the insertion section is disposed on an extended line of the central axis of the first arm by the fourth arm.

20. An observation system according to claim 17, wherein the switching mechanism comprises a brake for link, which is disposed on at least one of connecting portions between the arms among the first to sixth arms and which is switchable between a braking-off state to allow deformation of the first and second parallelogram links and a braking-on state to control the deformation.

21. An observation system according to claim 20, wherein the switching mechanism comprises:
a brake for vertical movement, which is disposed in the vertical movement mechanism and which is switchable between a braking-off state to allow movement of the observation device and the display device in a vertical direction and a braking-on state to control the movement;

a brake for horizontal movement, which is disposed in the horizontal movement mechanism and which is switchable between a braking-off state to allow movement of the observation device and the display device in a horizontal direction and a braking-on state to control the movement; and a brake for inclination, which is disposed in the inclination mechanism and which is switchable between a braking-off state to allow inclination of the observation device and the display device and a braking-on state to control the inclination.

22. An observation system according to claim 21, wherein the fourth arm comprises a switch capable of switching the braking-off state and the braking-on state of the brakes for link, vertical movement, horizontal movement, and inclination.

23. An observation system according to claim 22, wherein a switch capable of switching the braking-off state and the braking-on state of at least one of the brakes for link, vertical movement, horizontal movement, and inclination is disposed in the vicinity of the display device.

24. An observation system according to claim 21, wherein a switch capable of switching the braking-off state and the braking-on state of the brakes for link, vertical movement, horizontal movement, and inclination is disposed in the vicinity of the observation device.

25. An observation system according to claim 24, wherein a switch capable of switching the braking-off state and the braking-on state of at least one of the brakes for link, vertical movement, horizontal movement, and inclination is disposed in the vicinity of the display device.

26. An observation system comprising:
an observation device including an optical objective system for observation of an object;
an image pickup device which picks up an optical image incident upon the optical objective system of the observation device;
a display device which is electrically connected to the image pickup device and which displays the optical image picked up by the image pickup device; and
at least one holding mechanism including a moving mechanism which holds the observation device and the display device and which moves one of the observation device and the display device in conjunction with movement of the other device, and a switching mechanism capable of switching the observation device and the display device to a state in which the devices are movable by the moving mechanism and a state in which the devices are fixable in positions moved by the moving mechanism, wherein the holding mechanism comprises:
a first holding device which holds the observation device; and
a second holding device which holds the display device,
wherein the moving mechanism of the first holding device comprises:
a first vertical movement mechanism capable of moving the observation device in the vertical direction;
a first horizontal movement mechanism capable of moving the observation device in the horizontal direction;
a first inclination mechanism which inclines the observation device; and
a first equivalent movement mechanism in which the observation device is disposed, and the moving mechanism of the second holding device comprises:
a second vertical movement mechanism capable of moving the display device in the vertical direction;
a second horizontal movement mechanism capable of moving the display device in the horizontal direction;
a second inclination mechanism which inclines the display device; and
a second equivalent movement mechanism in which the display device is disposed and which moves the display device equivalently to the movement of the observation device by the first equivalent movement mechanism.

27. An observation system according to claim 26, wherein the first equivalent movement mechanism comprises a parallel link mechanism.

28. An observation system according to claim 27, wherein the parallel link mechanism comprises:
a first arm comprising one end portion and the other end portion, the one end portion being connected to the first inclination mechanism;
a second arm comprising an upper end portion and a lower end portion, the lower end portion being connected to the other end portion of the first arm;
a third arm comprising one end portion and the other end portion, the one end portion being connected to the upper end portion of the second arm, the third arm being disposed in parallel with the first arm;
a fourth arm comprising an upper end portion, and a lower end portion which holds the observation device, the upper end portion being connected to the other end portion of the third arm, the fourth arm being disposed in parallel with the second arm;
a fifth arm comprising an upper end portion and a lower end portion, the lower end portion being connected between the one end portion and the other end portion of the first arm, the fifth arm being disposed in parallel with the second arm; and
a sixth arm comprising one end portion and the other end portion, the one end portion being connected to the upper end portion of the fifth arm, the other end portion being connected to the fourth arm, the one end portion and the other end portion being connected between the upper and lower end portions of the second arm, the sixth arm being disposed in parallel with the first arm.

29. An observation system according to claim 28, wherein the switching mechanism comprises a brake for link, which is disposed on at least one of connecting portions between the arms among the first to sixth arms and which is switchable between a braking-off state to allow deformation of the parallel link mechanism and a braking-on state to control the deformation.

30. An observation system according to claim 29, wherein the switching mechanism further comprises:
a first brake for vertical movement, which is disposed in the first vertical movement mechanism and which is switchable between a braking-off state to allow movement of the observation device in the vertical direction and a braking-on state to control the movement;
a first brake for horizontal movement, which is disposed in the first horizontal movement mechanism and which is switchable between a braking-off state to allow movement of the observation device in the horizontal direction and a braking-on state to control the movement; and
a first brake for inclination, which is disposed in the first inclination mechanism and which is switchable between a braking-off state to allow inclination of the observation device and a braking-on state to control the inclination.

31. An observation system according to claim 30, wherein the fourth arm comprises a switch capable of switching the first brakes for link, vertical movement, horizontal movement, and inclination to the braking-off state and the braking-on state.

32. An observation system according to claim 31, wherein a switch capable of switching at least one of the first brakes for link, vertical movement, horizontal movement, and inclination to the braking-off state and the braking-on state is disposed in the vicinity of the display device.

33. An observation system according to claim 30, wherein a switch capable of switching the first brakes for link, vertical movement, horizontal movement, and inclination to the braking-off state and the braking-on state is disposed in the vicinity of the observation device.

34. An observation system according to claim 33, wherein a switch capable of switching at least one of the first brakes for link, vertical movement, horizontal movement, and inclination to the braking-off state and the braking-on state is disposed in the vicinity of the display device.

35. An observation system according to claim 27, wherein the second equivalent movement mechanism comprises a parallel link mechanism.

36. An observation system according to claim 35, wherein the parallel link mechanism of the second equivalent movement mechanism comprises:
   a first arm comprising one end portion and the other end portion, the one end portion being connected to the second inclination mechanism;
   a second arm comprising an upper end portion and a lower end portion, the lower end portion being connected to the other end portion of the first arm;
   a third arm comprising one end portion and the other end portion, the one end portion being connected to the upper end portion of the second arm, the third arm being disposed in parallel with the first arm;
   a fourth arm comprising an upper end portion, and a lower end portion which holds the display device, the upper end portion being connected to the other end portion of the third arm, the fourth arm being disposed in parallel with the second arm;
   a fifth arm comprising an upper end portion and a lower end portion, the lower end portion being connected between the one end portion and the other end portion of the first arm, the fifth arm being disposed in parallel with the second arm; and
   a sixth arm comprising one end portion and the other end portion, the one end portion being connected to the upper end portion of the fifth arm, the other end portion being connected to the fourth arm, the one end portion and the other end portion being connected between the upper and lower end portions of the second arm, the sixth arm being disposed in parallel with the first arm.

37. An observation system according to claim 36, wherein the switching mechanism comprises a brake for link, which is disposed on at least one of connecting portions between the arms among the first to sixth arms and which is switchable between a braking-off state to allow deformation of the link mechanism and a braking-on state to control the deformation.

38. An observation system according to claim 37, wherein the switching mechanism further comprises:
   a second brake for vertical movement, which is disposed in the first vertical movement mechanism and which is switchable between a braking-off state to allow movement of the observation device in the vertical direction and a braking-on state to control the movement;
   a second brake for horizontal movement, which is disposed in the first horizontal movement mechanism and which is switchable between a braking-off state to allow movement of the observation device in the horizontal direction and a braking-on state to control the movement; and
   a second brake for inclination, which is disposed in the first inclination mechanism and which is switchable between a braking-off state to allow inclination of the observation device and a braking-on state to control the inclination.

39. An observation system according to claim 38, wherein the fourth arm comprises a switch capable of switching the second brakes for link, vertical movement, horizontal movement, and inclination to the braking-off state and the braking-on state.

40. An observation system according to claim 39, wherein a switch capable of switching at least one of the second brakes for link, vertical movement, horizontal movement, and inclination to the braking-off state and the braking-on state is disposed in the vicinity of the display device.

41. An observation system according to claim 38, wherein a switch capable of switching the second brakes for link, vertical movement, horizontal movement, and inclination to the braking-off state and the braking-on state is disposed in the vicinity of the observation device.

42. An observation system according to claim 41, wherein a switch capable of switching at least one of the second brakes for link, vertical movement, horizontal movement, and inclination to the braking-off state and the braking-on state is disposed in the vicinity of the display device.

43. An observation system comprising:
   an observation device including an optical objective system for observation of an object;
   an image pickup device which picks up an optical image incident upon the optical objective system of the observation device;
   a display device which displays an observation image picked up by the image pickup device;
   a first holding section which holds the observation device;
   a second holding section which holds the display device;
   a moving mechanism which includes a first moving mechanism in which the first holding section is disposed and a second moving mechanism in which the second holding section is disposed, the moving mechanism being effective to move one of the observation device and the display device in conjunction with movement of the other device; and
   a switching mechanism capable of switching the observation device and the display device to a state in which the devices are movable by the moving mechanism and a state in which the devices are fixable in positions moved by the moving mechanism.

44. An observation system according to claim 43, wherein the moving mechanism comprises:
   a vertical movement mechanism capable of moving the observation device and the display device in a vertical direction;
   a horizontal movement mechanism capable of moving the observation device and the display device in a horizontal direction;
   an inclination mechanism which inclines the observation device in the vertical direction and which inclines the display device with respect to a horizontal plane; and
   an equivalent movement mechanism in which the observation device and the display device are mutually equivalently moved.

45. An observation system according to claim 44, wherein the equivalent movement mechanism comprises a parallel link mechanism including at least two parallelogram links.

46. An observation system according to claim 43, wherein the observation device comprises an insertion section of an endoscope, and the insertion section comprises a bendable portion.

47. An observation system according to claim 46, wherein a coupling mechanism is disposed between the insertion section and the display device, in which the bendable portion is bent with the movement of the display device and the display device is moved with the bending of the bendable portion.

48. An observation system according to claim 43, wherein the observation device comprises an electronic image microscope.

49. An observation system according to claim 48, wherein the electronic image microscope comprises a stereoscopic observation mechanism.

50. An observation system comprising:

an observation device including an optical objective system for observation of an object;

an image pickup device which picks up an optical image incident upon the optical objective system of the observation device;

a display device which displays an observation image picked up by the image pickup device;

a first holding section which holds the observation device;

a second holding section which holds the display device;

a moving mechanism in which the first and second holding sections are disposed and which moves one of the observation device and the display device in conjunction with movement of the other device; and a switching mechanism capable of switching the observation device and the display device to a state in which the devices are movable by the moving mechanism and a state in which the devices are fixable in positions moved by the moving mechanism, wherein the moving mechanism comprises:

a vertical movement mechanism capable of moving the observation device and the display device in a vertical direction;

a horizontal movement mechanism capable of moving the observation device and the display device in a horizontal direction;

an inclination mechanism which inclines the observation device in the vertical direction and which inclines the display device with respect to a horizontal plane; and an equivalent movement mechanism in which the observation device and the display device are mutually equivalently moved, wherein the equivalent movement mechanism comprises a parallel link mechanism including at least two parallelogram links, wherein the parallel link mechanism comprises:

a first arm comprising one end portion and the other end portion, the one end portion being rotatably connected to the inclination mechanism;

a second arm comprising an upper end portion and a lower end portion, the lower end portion being connected to the other end portion of the first arm;

a third arm comprising one end portion and the other end portion, the one end portion being connected to the upper end portion of the second arm, the third arm being disposed in parallel with the first arm;

a fourth arm comprising an upper end portion, and a lower end portion which holds the observation device, the upper end portion being connected to the other end portion of the third arm, the fourth arm being disposed in parallel with the second arm;

a fifth arm comprising an upper end portion and a lower end portion, the lower end portion being connected between the one end portion and the other end portion of the first arm, the fifth arm being disposed in parallel with the second arm; and a sixth arm comprising one end portion and the other end portion, the one end portion being connected to the upper end portion of the fifth arm, the other end portion being connected to the fourth arm, the one end portion and the other end portion being connected between the upper and lower end portions of the second arm, the sixth arm being disposed in parallel with the first arm.

51. An observation system according to claim 50, wherein the display device is disposed on a connecting portion of the other end portion of the first arm with the lower end portion of the second arm, the observation device comprises an insertion section of an endoscope, and the optical objective system of the insertion section is disposed on an extended line of a central axis of the first arm by the fourth arm, and an optical axis of an optical image between the optical objective system and the image pickup device is in a vertical state with respect to a display surface of the display device.

52. An observation system comprising:

an observation device including an optical objective system for observation of an object;

an image pickup device which picks up an optical image incident upon the optical objective system of the observation device;

a display device which displays an observation image picked up by the image pickup device;

a first holding section which holds the observation device;

a second holding section which holds the display device;

a moving mechanism in which the first and second holding sections are disposed and which moves one of the observation device and the display device in conjunction with movement of the other device; and a switching mechanism capable of switching the observation device and the display device to a state in which the devices are movable by the moving mechanism and a state in which the devices are fixable in positions moved by the moving mechanism, wherein the moving mechanism comprises a first movable member in which the first holding section is disposed, a second movable member in which the second holding section is disposed, and a movable member conjunction mechanism which moves at least one of the first and second movable members in conjunction with the movement of the other movable member.

53. An observation system according to claim 52, wherein the movable member conjunction mechanism comprises a control device which controls a display surface of the display device and an optical axis of the observation device in a state in which the display surface and the optical axis cross each other at right angles.

54. An observation system according to claim 53, wherein the control device comprises:

a first detection section which detects posture of the observation device;

a second detection section which detects posture of the display device;

a calculation section which calculates relative positions of the observation device and the display device from detected amounts detected by the first and second detection sections; and a posture adjustment section which adjusts the posture of at least one of the observation device and the display device in accordance with a calculation result of the calculation section.

55. An observation system according to claim 54, wherein the posture adjustment section comprises a motor being controlled by rotation number in accordance with the calculation result of the calculation section.

56. An observation system according to claim 54, wherein the first detection section comprises a plurality of encoders, disposed in the moving mechanism, to detect the movement amount of the observation device, and the second detection section comprises a plurality of encoders, disposed in the moving mechanism, to detect the movement amount of the display device.

57. An observation system according to claim 53, wherein the control device comprises:

a first detection section which detects posture of the observation device;

a second detection section which detects posture of the display device;

a relative position calculation section which calculates relative positions of a view field direction of the image pickup device and a view field direction displayed in the display device from detected amounts detected by the first and second detection sections; and an image rotation section which rotates an image displayed in the display device in accordance with a calculation result from the relative position calculation section.

58. An observation system according to claim 57, wherein the first detection section comprises a plurality of encoders, disposed in the moving mechanism, to detect the movement amount of the observation device, and the second detection section comprises a plurality of encoders, disposed in the moving mechanism, to detect the movement amount of the display device.

\* \* \* \* \*